US006264601B1

(12) United States Patent
Jassawalla et al.

(10) Patent No.: US 6,264,601 B1
(45) Date of Patent: Jul. 24, 2001

(54) IMPLANTABLE VENTRICULAR ASSIST DEVICE

(75) Inventors: Jal S. Jassawalla, Orinda; David H. LaForge, Kensington; Phillip J. Miller, Berkeley, all of CA (US)

(73) Assignee: World Heart Corporation, Oakland, CA (US)

( * ) Notice: Subject to any disclaimer, the term of this patent is extended or adjusted under 35 U.S.C. 154(b) by 0 days.

(21) Appl. No.: 09/285,933

(22) Filed: Apr. 2, 1999

(51) Int. Cl.[7] .................................................. A61M 1/12
(52) U.S. Cl. ...................................... 600/16; 623/3.17
(58) Field of Search ..................... 600/16, 17; 623/3.1, 623/3.11, 3.16, 3.17, 3.18, 3.19–3.23

(56) References Cited

U.S. PATENT DOCUMENTS

| | | | |
|---|---|---|---|
| 3,842,440 | * 10/1974 | Karlson | ................................... 600/16 |
| 4,046,137 | 9/1977 | Curless et al. . | |
| 4,091,471 | 5/1978 | Richter . | |
| 4,204,524 | 5/1980 | Martin et al. . | |
| 4,468,177 | 8/1984 | Strimling . | |
| 4,512,726 | 4/1985 | Strimling . | |
| 4,547,911 | 10/1985 | Strimling . | |
| 4,968,293 | 11/1990 | Nelson . | |
| 4,969,864 | 11/1990 | Schwarzmann et al. . | |
| 5,006,104 | 4/1991 | Smith et al. . | |
| 5,011,380 | 4/1991 | Kovacs . | |
| 5,133,743 | 7/1992 | Strimling et al. . | |
| 5,211,659 | 5/1993 | Strimling et al. . | |
| 5,282,850 | 2/1994 | Davidson . | |
| 5,810,708 | 9/1998 | Woodard et al. . | |

* cited by examiner

Primary Examiner—George R. Evanisko
(74) Attorney, Agent, or Firm—Coudert Brothers

(57) ABSTRACT

An implantable ventricular assist device (VAD) has a small size to provide full-implantable capabilities. The VAD has two variable-volume chambers and an actuator for expelling blood from the chambers in sequence and to a common outlet, thus operating as a positive-displacement pump. The variable-volume chambers may be flexible sacs and the pump is operable at a substantially continuous flow, such as during the systolic phase of the assisted ventricle. A method of operation includes operating the pump at a first frequency during systole and a second lower frequency during diastole. The VAD pump includes a pair of coils housed within a frame and disposed in a spaced relationship to generate a coil flux through a pair of poles. A plate including an armature and a magnet is disposed within the frame such that the armature is between the poles and the magnet is between the coils. Gaps are defined between the armature and each of the poles and the coil flux displaces the armature across the gap. The coil flux follows a donut-shaped path including the frame, one of the poles, one of the gaps, the armature, the other the gap, and the other the pole, and no coil flux passes through the magnet. The magnet is not subject to depolarization and may be made substantially smaller than those of conventional devices. The magnet generates a bias flux that offsets a portion of the coil flux around the frame. A spring may be provided to counteract the unstable action of the bias magnet. The volume of the chambers is a fraction of the ventricular volume, and may be about 20 ml. To pump a typical 80-ml volume of a left ventricle, the controller may activate the coils four times during systole, or once every 40 msec.

44 Claims, 10 Drawing Sheets

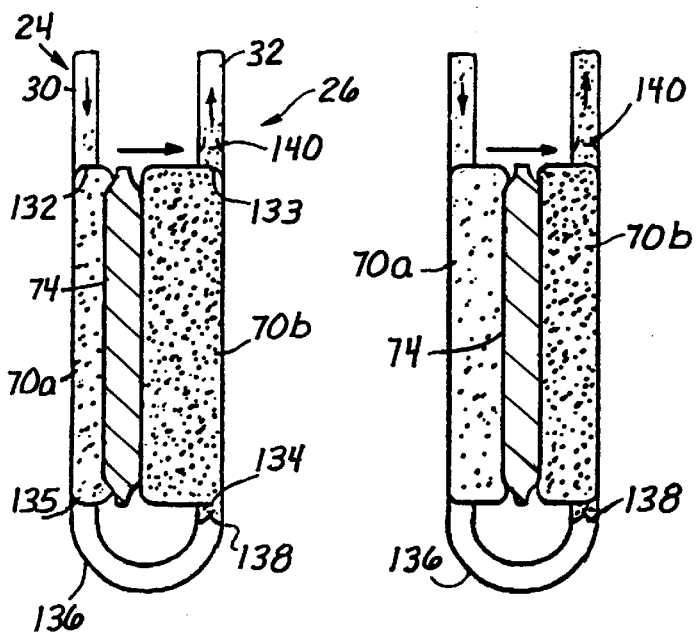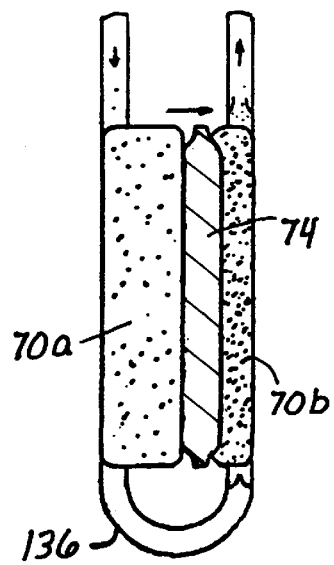
Fig. 10A  Fig. 10B  Fig. 10C
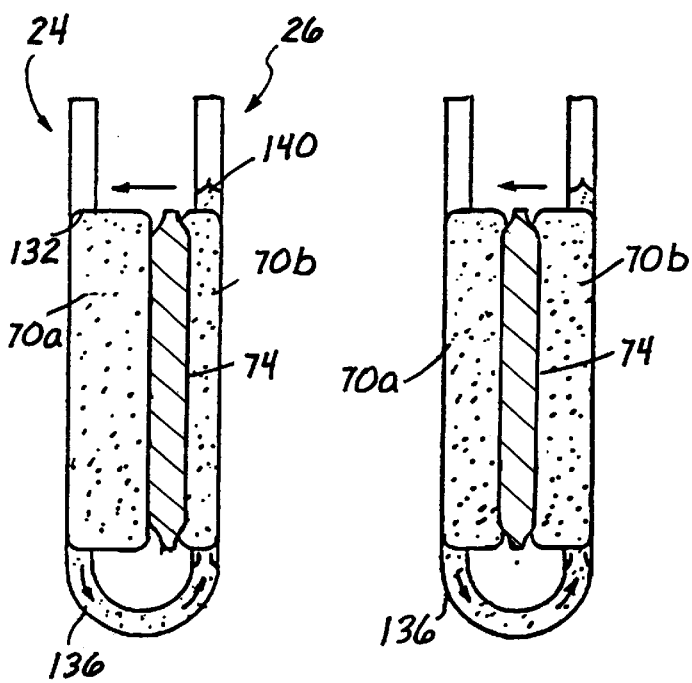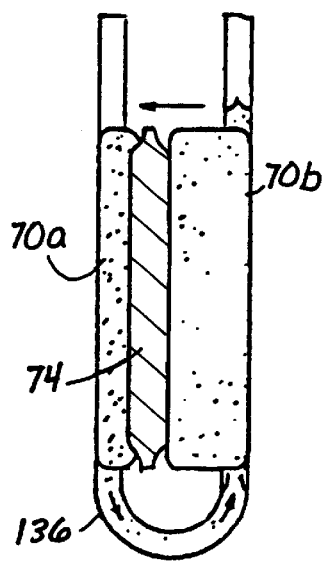
Fig. 10D  Fig. 10E  Fig. 10F

IMPLANTABLE VENTRICULAR ASSIST DEVICE

BACKGROUND OF THE INVENTION

1. Field of the Invention

The present invention relates to devices and associated methods for pumping fluids, for example, blood. More particularly, the present invention relates to implantable ventricular assist devices (VADs) that are utilized to replace the function of either the right ventricle or the left ventricle, or both, of the heart. The ventricular assist devices of the present invention include certain features that relate in the art to electric pulsatile devices.

2. Description of the Related Art

Four hundred thousand new cases of congestive heart failure are diagnosed in the United States annually, a number which will only rise in the foreseeable future with the aging of the baby-boom generation. According to the Framingham Heart Study, the five-year mortality rate for patients with congestive heart failure was 75 percent in men and 62 percent in women. Standard medical and surgical therapies benefit only a small percentage of patients with ventricular dysfunction. Potential cardiac transplant recipients with hemodynamic instability may receive temporary mechanical circulatory support, such as an implantable blood pump, as a bridge to cardiac transplantation. Moreover, estimates in the field suggest that 17,000 to 66,000 patients each year in the United States may benefit from a permanent implantable blood pump.

The ventricular assist device (VAD) is a blood pump designed to assist or replace the function of either ventricle, or both ventricles, of the heart. A right ventricular assist device (RVAD) supports pulmonary circulation by receiving or withdrawing blood from the right ventricle and returning it to the pulmonary artery. A left ventricular assist device (LVAD) supports systemic perfusion by receiving or withdrawing blood from the left ventricle (or left atrium) and returning it to the aorta. A biventricular assist device (BVAD) supports both ventricles of the heart. Ventricular assist devices may be either implantable or extracorporeal, with implantable VADs positioned intracorporeally in the anterior abdominal wall or within a body cavity (other than the pericardium) and with extracorporeal VADs located paracorporeally, along the patient's anterior abdominal wall, or externally at the patient's bedside.

The first ventricular assist devices attempted to mimic the pulsatile flow of the natural left ventricle by utilizing flexible chambers with volumes approximately equal to the volume of the respective ventricle being assisted. The typical volume of blood expelled by the left ventricle of an adult is between 70–90 ml, but may range from 40–120 ml. The chambers are expanded and contracted, much like a natural ventricle, to alternately receive and expel blood. One way valves at the inlet and outlet ports of the chambers ensured one way flow therethrough.

So-called "pulsatile pumps" may include one or a pair of driven plates for alternately squeezing and expanding flexible chambers. The flexible chambers typically comprise biocompatible segmented polyurethane bags or sacs. The blood sac and drive mechanism are mounted inside a compact housing that is typically implanted in the patient's abdomen. A controller, backup battery, and main battery pack are electrically connected to the drive mechanism. Even the most basic drive mechanisms of the prior art are relatively complex and expensive, and typically incorporate some type of mechanical cam, linkage, or bearing arrangement subject to wear.

Because of the varying volume of the blood sac within the rigid encapsulation housing of pulsatile pumps, accommodation must be made for the air displaced thereby. Some devices utilize a percutaneous tube vented to the atmosphere, which is a simple approach but has the disadvantage of a skin penetration and associated infection risk. Another approach, proposed for fully-implantable VAD systems, is to use a volume compensator. This is a flexible chamber, implanted in the thoracic cavity adjacent to the lungs and communicating with the air space within the housing and outside the blood sac via an interconnecting tube. As the blood sac expands with incoming blood, air is displaced from the housing to the volume compensator. Conversely, expulsion of blood from the blood sac creates a negative pressure within the housing and pulls air from the volume compensator. While eliminating the infection risk of the percutaneous vent, the volume compensator poses certain challenges: increased system complexity, an additional implanted component and potential site of infection, maintaining long-term compliance of the implanted volume compensator sac, problems associated with gas diffusion in or out of the enclosed volume, and problems associated with changes in ambient pressure, such as experienced during a plane flight.

One example of an electric pulsatile blood pump is the Novacor N 100 left ventricular assist system (Novacor Division, Baxter Healthcare Corporation, Oakland, Calif.). This system contains a single polyurethane blood sac with a nominal stroke volume of 70 ml that is compressed by dual symmetrically opposed pusher plates in synchronization with the natural left ventricle contraction. The pusher plates are actuated by a spring-decoupled solenoid energy converter. The blood pump and energy converter are contained within a housing that is implanted in the patient's abdomen. The N 100 is a tethered system employing a percutaneous vent tube carrying power and control wires.

Biventricular heart assist devices employ two pumps, with the input of each connected to separate pumping chambers of the heart. For instance, U.S. Pat. No. 4,468,177 to Strimling discloses a diaphragm pump having a piston that is moveable within a chamber to reduce the volume of a chamber on one side while simultaneously enlarging the volume of a second chamber on the opposite side. Another patent to Strimling, U.S. Pat. No. 4,547,911, discloses an implantable heart pump having two pusher plates driven synchronously between two variable-volume chambers at a multiple of the natural rhythm of the heart. Each of the Strimling devices may function either as a BVAD heart pump with each chamber communicating separately with a respective ventricle of the heart, or as a single ventricle-assist pump wherein the two chambers are connected in series with a shunt therebetween.

In recent years there has been increased study into the potential of using rotary pumps (centrifugal or axial) for ventricular assist. These pumps employ fast-moving impellers to impart forward flow to the blood. The impellers are either supported by bearings or are magnetically levitated. A significant advantage of rotary pumps is their relatively compact size and low cost. In addition, the pressure difference maintained by the impeller eliminates the need for one-way valves as in pulsatile pumps. Finally, no venting or volume compensator is necessary.

The use of rotary pumps has generated a significant amount of interest in this field, but as yet many drawbacks prevent general acceptance. For instance, bearing-supported impellers usually require lubrication that must be absolutely kept out of contact with the blood, thus requiring seals that remain highly effective for extended periods. In some designs, the bearings are within the pump housing in contact with blood, which is then used as the lubricating fluid and may be subject to degradation. In addition, the heat generated by some bearing configurations may adversely affect the blood. Some designs eschew bearings altogether and instead utilize magnetically levitated impellers. However, these are relatively complex and sometimes unstable. A safety issue with rotary pumps is their non-occlusive character which provides a shunt path for blood regurgitation if the impeller is not rotating. That is, the one-way valves in pulsatile pumps ensure a uni-directional pathway through which blood is propelled, and prevent regurgitation from the arterial vessel if the device shuts off or fails. The natural ventricle can thus function as a back-up perfusion system, bypassing the pump circuit. If the impeller in a rotary pump stops, however, a flow path is created permitting blood from the arterial vessel to be shunted through the pump, thus seriously impairing the back-up capability of the natural ventricle. To prevent this situation, a one-way valve or occluder of some sort must be provided at the rotary pump outflow. A still further issue with rotary pumps, as yet to be resolved, is the efficacy of the continuous flow of blood provided thereby. There are studies on both sides which either favor pulsatile flow, or at least suggest no negative side effects from continuous flow.

In view of the foregoing, there is an ongoing need in the art to improve upon conventional ventricular assist devices. For example, reductions in size and the elimination of the volume compensator would be advantageous to facilitate full implantation of a device. In addition, pulsatile flow without the disadvantages of conventional devices is a goal. Further, a device that is low in cost but does not have the disadvantages of rotary pumps would be advantageous for long-term use. Accordingly, there remains a need in the art for a small, efficient, atraumatic, and fully implantable ventricular assist device that overcomes the deficiencies of conventional devices.

SUMMARY OF THE INVENTION

The present invention provides a pumping system for assisting the ventricles of the heart. The pumping system of the invention has a relatively small size and is free of many disadvantages inherent in conventional blood pumps. In addition, the pumping system of the present invention can provide pulsatile flow of varying degrees and duration, even up to continuous flow, in a small fully implantable and relatively mechanically simple device. Desirably, the pumping system provides intermittent periods of substantially continuous flow during systole. Accordingly, the present invention provides a pumping system that is small, efficient, atraumatic, and fully implantable while overcoming the deficiencies of conventional devices.

In one aspect, the present invention provides a ventricular assist device comprising an implantable housing and a pair of variable-volume chambers mounted therein, each of the chambers having an inlet port and an outlet port. At least one ventricular outflow conduit is adapted to be connected between the ventricle and the inlet ports. An actuator is disposed within the housing to alternately contract one of the variable-volume chambers while expanding the other, and vice versa, to provide a positive displacement pump. Preferably, the actuator comprises a movable plate having a permanent magnet thereon, and a portion of the housing is magnetically permeable so that the plate is unstable in a central position between the two variable-volume chambers, and is biased toward one or the other upon a slight displacement in that direction. Furthermore, the device preferably includes electromagnetic coils mounted in the housing and situated so as to generate a coil flux path through the housing and through a magnetically permeable portion of the movable plate. In this manner, the movable plate functions as an armature and the coil flux displaces the armature toward one of the two variable volume chambers depending on the current direction through the coil. In addition, the coil flux preferably does not travel through the permanent magnet which might otherwise depolarize it.

According to one particular aspect of the invention, the pumping system is configured as a ventricular assist device including a pump and cannulation for connecting the pump to the cardiovascular system of a patient. The pump includes a pair of compressible chambers and electro-magnetic structure having a frame, a pair of coils, and a plate. The coils are disposed in a spaced relationship within the frame. The coils generate coil flux and define a pair of respective poles when electrically activated. The plate has an armature and a magnet and is disposed within the frame such that the armature is between the poles and the magnet is between the coils. The magnet generates bias flux. Each chamber is disposed between the plate and one of the coils. Each of the chambers has a volume substantially less than the ejection volume of the ventricle, preferably about one-quarter of the ejection volume of the ventricle. For example, in an LVAD in accordance with the present invention, assuming that the ejection volume of a typical left ventricle is about 80 ml, the volume of each chamber may be on the order of about 20 ml.

The present invention also provides a method of ventricular assist using a ventricular assist pump including two pumping chambers, valved inlet and outlet conduits for each chamber, and an actuator. The method includes directing an inflow of blood from a single ventricle to both of the chambers, and actuating the pumping chambers with the actuator during a systolic phase of the assisted ventricle to alternately expel blood from one of the chambers while drawing blood into the other of the chambers.

Another aspect of the invention is a method of ventricular assist using a positive displacement pulsatile pump having two variable-volume chambers each with a volume less than about one-half of the ejection volume of the ventricle. The method includes implanting the pump in a patient so as to be in fluid communication with the blood circulatory system, actuating the pump during systole to provide substantially continuous flow output and propel the ventricular ejection volume into an arterial vessel, and resting the pump during a diastolic phase of the assisted ventricle.

One of the advantages of the pumping system of the present invention is that there is no need for a volume compensator or a compliance chamber. Accordingly, the overall size and complexity of the system is substantially reduced. It follows that system cost is reduced while system reliability and patient acceptability are increased. In addition to the compliance chamber, bearings and other blood-damaging components are eliminated. This feature is advantageous not only in reducing complexity and cost but also in increasing the long-term period for which the pumping system may be implanted in a patient.

Another advantage of the present invention is that the pumping system provides substantially pulsatile flow. As the volume of each chamber is, for example, about one-quarter the ejection volume of the ventricle, a controller of the pumping system may cause the coils to stroke the plate about 4 times during one beat of the heart (i.e., during systole or ventricular contraction). Accordingly, even employing chambers with a substantially reduced volume, the pumping system is able to keep up with the normal ejection volume of the ventricle. This pulsatile flow provided by the pump is substantially analogous to the blood flow out of a healthy ventricle. Alternatively, the pumping system may be operated continuously to provide substantially uniform flow.

According to another aspect of the invention, the flux generated by the coils follows a path including one of the poles, one of the gaps defined between the armature and the poles, the armature, the other gap, and the other pole such that the magnet is substantially free of the coil flux. One of the advantages of this feature of the invention is that the bias flux remains substantially constant, such that the magnet does not depolarize. Another advantage stemming from the bias magnet not being depolarized is that the bias magnet may be made relatively small, thereby further reducing the size and weight of the pump. For example, the pump, which may be substantially cylindrical, may have a diameter less than about 100 millimeter.

Other aspects, features, and advantages of the present invention will become apparent to those skilled in the art from a consideration of the following detailed description taken in conjunction with the accompanying drawings which illustrate, by way of example, the principles of the present invention in the context of a blood pump for left-ventricular assistance, but which are equally relevant to blood pumps for assisting the right or both ventricles, or in general to other devices for pumping fluid.

BRIEF DESCRIPTION OF THE DRAWINGS

FIGS. 10A to 10F are schematic views of the blood pump of FIG. 9, illustrating the variable-volume chambers of the pump operating in series.

DESCRIPTION OF THE PREFERRED EMBODIMENTS

Ventricular—assist System

Figure 1:
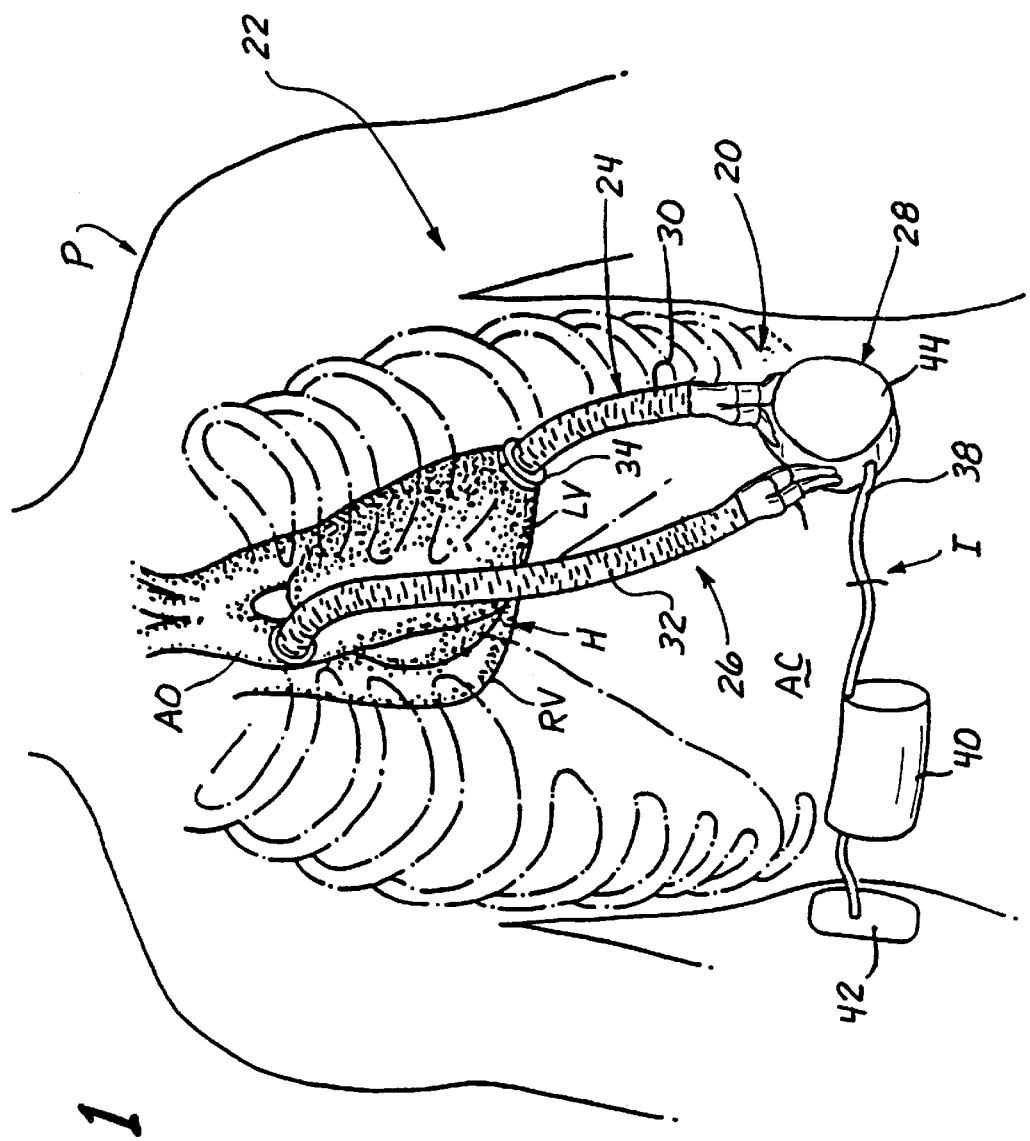
FIG. 1 is a perspective view of a ventricular assist system of the present invention connected to a heart of a patient (shown in phantom) for left ventricular assist.
Figure 2:
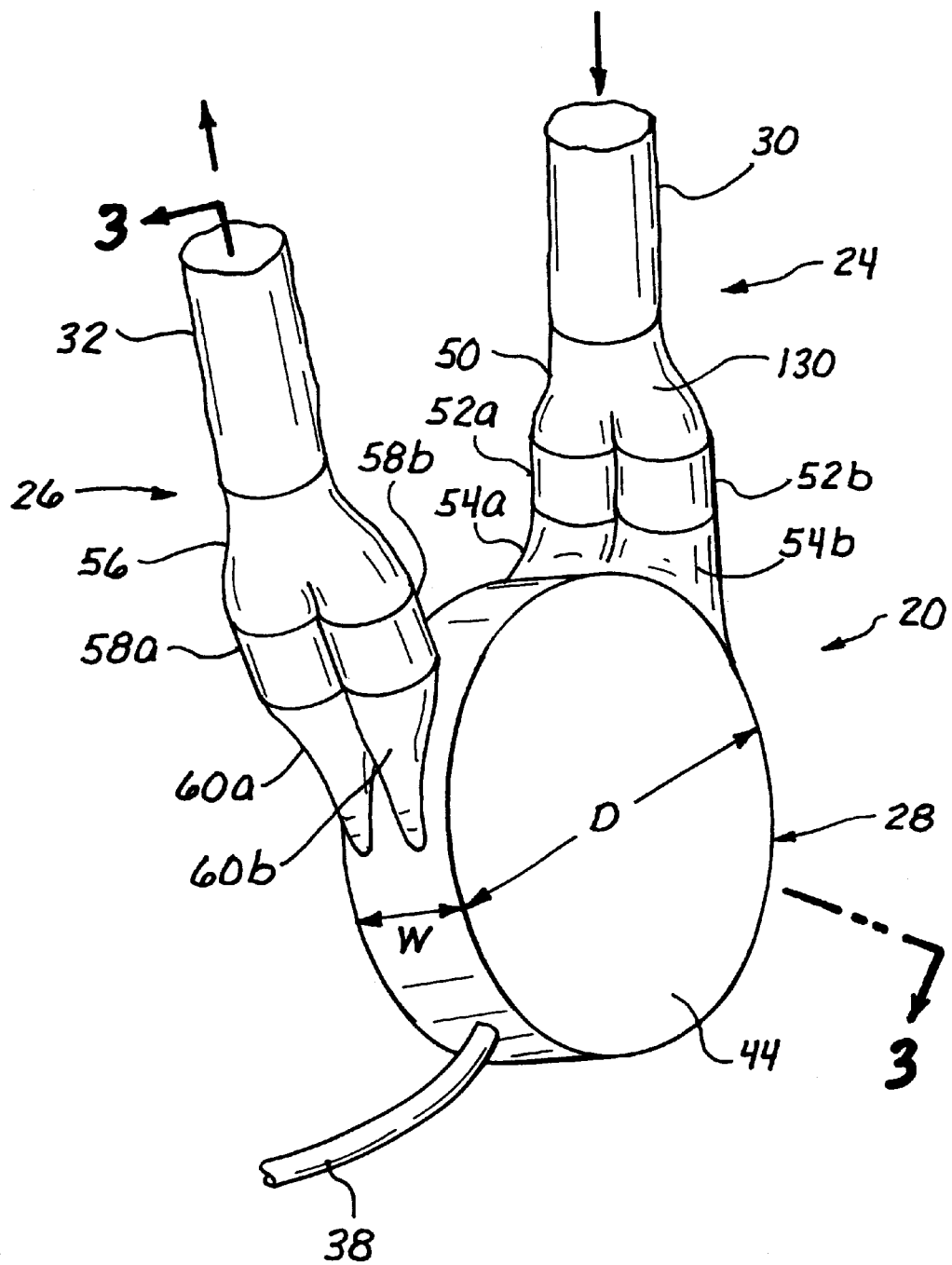
FIG. 2 is a perspective view of a blood pump of the ventricular assist system in which variable-volume chambers operate in parallel.

With reference first to FIG. 1, a living human host patient P is shown in fragmentary front elevational view, and with parts of the patient's anatomy shown in phantom or removed solely for better illustration of the salient features of the present invention. A pumping portion 20 of a ventricular assist system 22 is surgically implanted into the patient's abdominal cavity AC and connected to the heart H with cannulation. The cannulation includes an inlet conduit 24 communicating blood from the patient's left ventricle LV into the pumping portion 20, and an outlet conduit 26 communicating blood from the pumping portion 20 to the patient's aorta AO. As discussed in detail below, pumping portion 20 includes a blood pump 28, an exemplary embodiment of which is shown in FIG. 2.

For purposes of explanation and without limiting the scope of the present invention, exemplary ventricular assist system 22 is illustrated assisting the left ventricle LV of the heart of the patient P. In addition to being configurable as a left ventricular assist device (LVAD), the ventricular assist system 22 may also be configured to assist the right ventricle (RVAD), as well as both ventricles (biventricular assistance, or BVAD). Therefore, as a general matter, and except in reference to the illustrated LVAD, the source of blood for the ventricular assist system 22 may be termed the "assisted ventricle," while the destination of the pressurized blood will be designated the "arterial vessel."

Each of the conduits 24 and 26 include flexible segments 30 and 32 extending to the left ventricle LV and aorta AO, respectively. The inlet and outlet conduits 24 and 26 are attached to the natural tissue of the ventricle and the arterial vessel by sutures to establish and maintain blood flow, and may include appropriate structure for this purpose such as a sewing ring 34 for ventricular attachment. In any of the contemplated configurations of LVAD, RVAD, or BVAD, the inlet conduits are anastomosed to the respective ventricle, while the outlet conduits are anastomosed to the appropriate arterial vessel, which for left ventricular assist is typically the aorta AO and for right ventricular assist is typically the pulmonary artery. As will be explained below, the exemplary ventricular assist system 22 includes a single ventricular anastomosis branching to two input ports in the pumping portion 20, but those of skill in the art will realize that the device will function with two separate anastomoses. Likewise, the outlet conduit 26 is shown branched, but could remain as two separate conduits with separate arterial anastomoses. Details of the conduits 24, 26 may be shown and described in co-pending U.S. patent application Ser. No. 09/191,506, filed Nov. 13, 1998, the disclosure of which is expressly incorporated herein by reference.

With continued reference to FIG. 1, a power cable 38 extends from the pumping portion 20 outwardly of the patient's body via an incision I to a controller 40 and a power supply 42, such as a battery pack. Other means for powering the ventricular assist system 22 are known which do not require a cable through the skin, and the present invention is not so limited. The blood pump 28 necessarily includes a rigid housing 44 outwardly formed of a biocompatible coating such as a polymer or other suitable biocompatible material.

Positive—Displacement VAD

The pumping portion 20 of the system 22 is seen in greater detail in FIG. 2 connected to a branching structure of the conduits 24 and 26. More particularly, the flexible segment 30 connects to a bifurcated inlet conduit segment 50, which in turn connects to a pair of inlet branches 52a, 52b, each of which are placed in fluid communication with a separate inlet port 54a, 54b of the pumping portion 20. Likewise, the flexible segment 32 connects to a bifurcated outlet conduit segment 56, which in turn connects to a pair of outlet branches 58a, 58b, each of which are placed in fluid communication with a separate outlet port 60a, 60b of the pumping portion 20. As will be described below, the pump 28 includes a pair variable volume chambers operating in synchronization with one filling with blood, and the other expelling blood, thus resulting in a positive displacement pump. The branching structure of the conduits 24 and 26 enables this parallel pumping action with the common inlet source (tube 30) and common outlet destination (tube 32).

As seen in FIGS. 3 and 4A–4F, exemplary pump 28 includes a pair of variable-volume chambers 70, for example, a left chamber 70a and a right chamber 70b, each of which has a volume that is no more, and preferably less, than half the ejection volume of the ventricle being assisted; for example, in the illustrated setup, the volume of each chamber 70 may be on the order of one-quarter the volume of the left ventricle LV. In the illustrated embodiment, the chambers 70 are defined within the cavities of flexible sacs 72a, 72b that are preferably configured as relatively flat disk-shaped bags. It should be noted that other sac configurations are possible within the understanding of one skilled in the art, and also that variable-volume chambers may be defined by structures other than flexible sacs, such as piston-cylinder couples, moveable walls, etc. A number of features of the present invention can thus be transferred to other fluid propulsion arrangements, though the use of dual flexible sacs provides a number of significant advantages and is thus preferred.

The sacs 72a, 72b are disposed in parallel and spaced apart by an actuator plate 74. The actuator plate 74 is preferably affixed to the inwardly-facing flat surfaces of each sac 72 with, for example, adhesive. To accept and pump the ejection volume of the ventricle in full with the reduced-volume chambers 70, the blood pump 28 has a drive system that pumps the chambers 70 a plurality of times for each beat of the heart H and provides a substantially continuous flow of blood during such pumping. The drive system displaces the actuator plate 74 left and right to alternately compress each chamber 70. As shown more clearly in the simplified schematics of FIG. 4, the chambers 70 are connected in parallel so as to eject oxygenated blood into the arterial vessel during each stroke of the plate 74. This feature of the invention not only reduces the overall size of the blood pump 28 but also eliminates the need for a compliance chamber (or volume compensator), which will be discussed in detail below.

Figure 3:
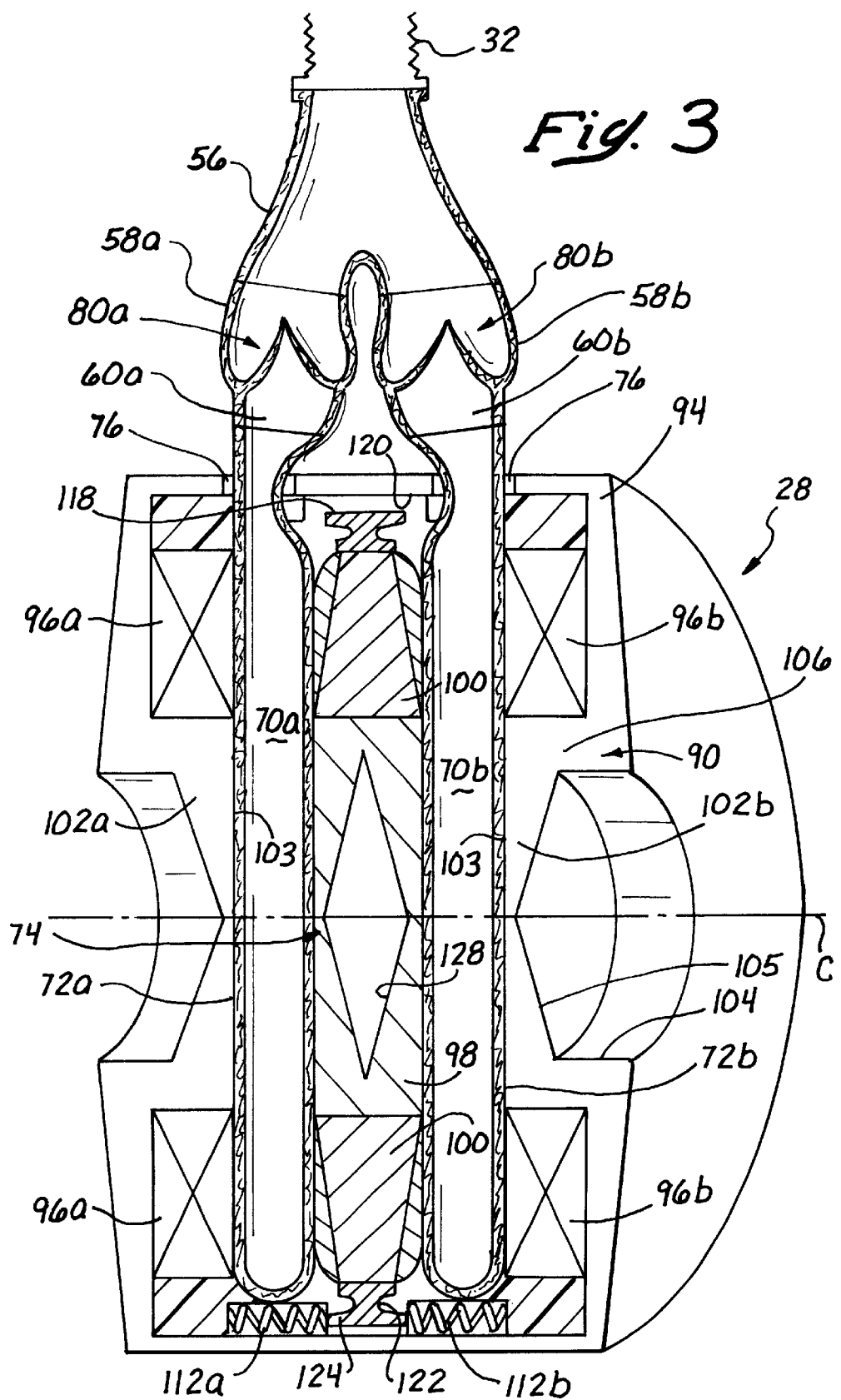
FIG. 3 is a cross-sectional view of an exemplary blood pump of the invention taken along line 3—3 of FIG. 2, FIGS. 4A to 4F are schematic views of a preferred configuration of pumping chambers of the present invention operating in parallel, particularly illustrating sequential stages in which each stroke is an ejection stroke.

The cross-section of FIG. 3 is taken across a midplane M of the pumping portion 20 except for the area at the top of FIG. 3 which is taken tangentially through the outlet conduit 26. That is, each of the inlet and outlet conduits 24, 26 extend generally tangentially from the cylindrical pumping portion 20. The configuration of the outlet ports 60a, 60b is seen in FIG. 3 and, though not apparent from the drawing, these also are disposed tangentially with respect to the disk-shaped sacs 72a, 72b. Likewise, the inlet ports 54a, 54b are tangential to the sacs 72a, 72b. The tangential orientation of the ports 54, 60 is believed to most effectively fill and flush blood to and from the chambers 70. The housing 44 includes appropriate inlet apertures (not shown) and outlet apertures 76 for receiving the inlet ports 54a, 54b and the outlet ports 60a, 60b, respectively. These apertures 76 are sealed about the ports 54, 60 to prevent fluid seepage therebetween.

As seen in detail in FIG. 3, each of the outlet branches 58a and 58b includes a pair of outlet valves 80a and 80b. Likewise, as seen in the schematic views of FIGS. 4A–4F, each of the inlet branches 52a, 52b, includes a pair of inlet valves 82a and 82b. The valves 80, 82 enable the positive-displacement pump to function as will be explained below. The valves 80, 82 are desirably polymeric or xenograft tissue valves, such as porcine aortic valves, although the present invention is not so limited. Details of various aspects of tissue valves are shown and described in U.S. Pat. No. 5,810,708, issued on Sep. 21, 1998, the disclosure of which is expressly incorporated herein by reference. The illustrated embodiment shows discrete branch segments 52, 58 disposed between the bifurcated inlet conduit segment 50 and respective ports 54, 60 which is a convenient arrangement for mounting of tissue valves. Alternatively, one or more of the bifurcated inlet conduit segment 50, branches 52, 58 and even ports 54, 60, may be integrally formed of a suitable polymer, for example, with the valves also being formed therein of the same or a different material.

With further reference to FIG. 3, exemplary pump 28 of the present invention may have a shoe 118 disposed between the bias magnet 100 and an inner surface 120 of the frame 94. The shoe 118 is shaped somewhat like an I-beam, with a narrow neck 122 and an outer rail 124. Without the narrow neck 122, and without the centering shear forces imposed on both sides by the elastic sacs 72, radial movement of the plate 74 would reduce the annular gap a (see FIG. 5A) consequently increasing the radial magnetic force which tends to displace the plate 74 over to that side, possibly into contact with the frame 94. In operation of the present embodiment, if the plate 74 shifts radially close to the inner surface 120 on any side, the neck 122 saturates with magnetic flux which limits the radial magnetic forces and thus halts further lateral displacement of the plate 74 which might otherwise tend to occur. Eventually, axial movement of the plate 74 and the centering shear force imposed by the flexible sacs 72 couple to re-center the plate.

Also shown in the exemplary embodiment of FIG. 3, the armature 98 has a diamond-shaped hollow center, indicated by reference numeral 128, which reduces the weight of the pump 28. More to the point, the hollow center 128 reduces the mass of the plate 74 which thus reduces the power (and battery size) needed to displace it, and in turn reduces the size of coils 96 required. The entire device can thus be reduced in size to further facilitate successful implantation.

Operation of Positive—Displacement VAD

As mentioned above, the drive system (a preferred embodiment of which is described below) displaces the actuator plate 74 left and right to alternately compress each variable-volume chamber 70. In a first stage of operation in FIG. 4A, the actuator plate 74 displaces to the right toward the right chamber 70b which is filled with oxygenated blood from the ventricle being assisted. The plate 74 compresses the right chamber 70b and ejects blood through outlet port 60b and outlet valve 80b and into the flexible outlet segment 32 for delivery to the arterial vessel. The plate 74 helps pull a reduced pressure in the left chamber 70a which in turn receives blood from the flexible inlet segment 30 through the left inlet valve 82a and left inlet port 54a. The left outlet valve 80a prevents blood from entering the left chamber 70a from the flexible outlet segment 32, and the right inlet valve 82b prevents blood from being ejected into the flexible inlet segment 30 when the plate 74 is moving to the right.

Figures 4A, 4B, 4C:
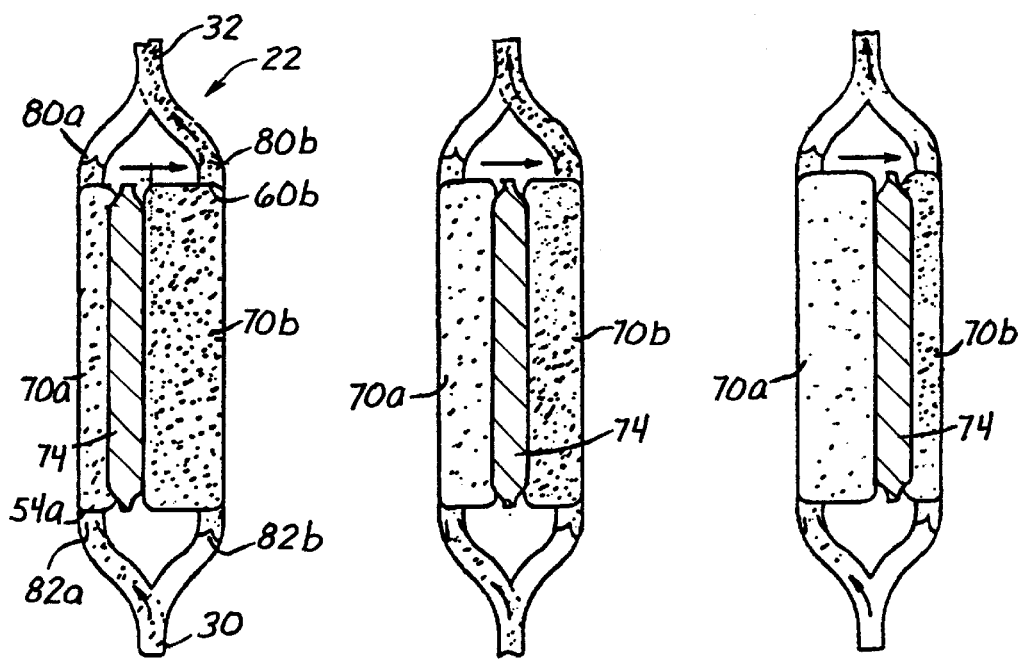

As the plate 74 continues to move to the right as shown in FIG. 4B, the left chamber 70a expands, thereby receiving blood from the ventricle being assisted. When the plate 74 has moved all the way to the right as shown in FIG. 4C, the right chamber 70b is compressed to a minimum volume while the left chamber 70a is expanded and filled with oxygenated blood from the assisted ventricle. The chambers 70 are substantially compressed to eject a majority of blood therein, but are not completely emptied to avoid contact between the inner surfaces of the sacs 72.

Figures 4D, 4E, 4F:
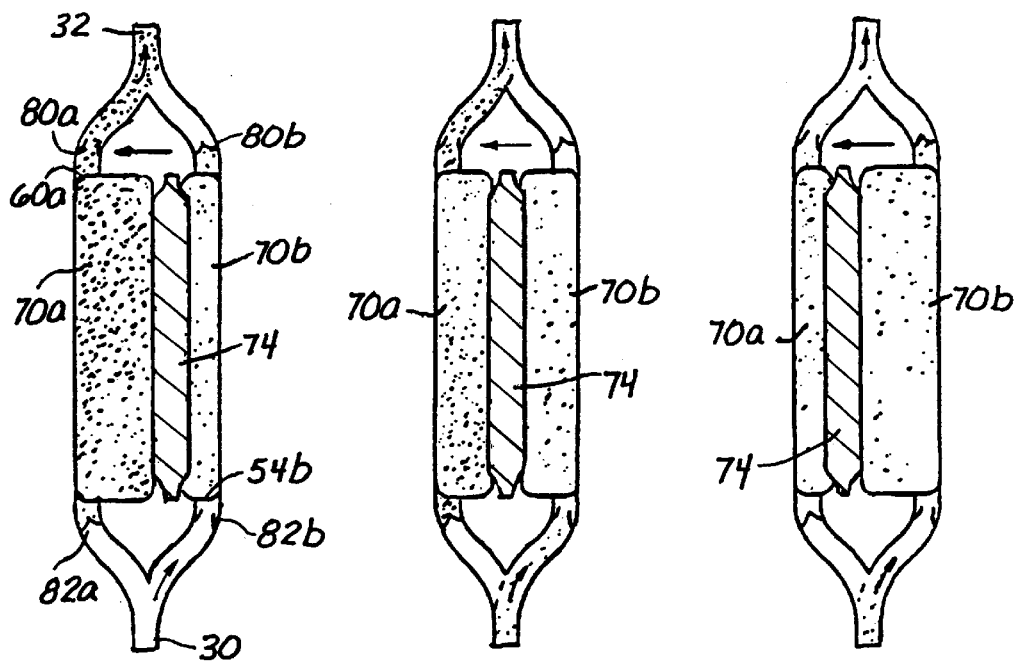

In the reverse sequence of FIGS. 4D–4F, the drive system displaces the plate 74 to the left to compress the left chamber 70a and eject blood through the left outlet port 60a and the left outlet valve 80a and into the flexible outlet segment 32 for delivery to the arterial vessel. The plate 74 helps pull a reduced pressure in the right chamber 70b which in turn receives blood from the flexible inlet segment 30 through the right inlet valve 82b and right inlet port 54b. When the plate 74 is moving to the left, the right outlet valve 80b prevents blood from entering the right chamber 70b from flexible outlet segment 32, and the left inlet valve 82a prevents blood from being ejected into the flexible inlet segment 30.

As the plate 74 continues to move to the left, the right chamber 70b expands, thereby receiving blood from the assisted ventricle. When the plate 74 has moved all the way to the left as shown in FIG. 4F, the left chamber 70a is compressed to a minimum volume while the right chamber 70b is expanded and filled with oxygenated blood from the assisted ventricle.

Preferred Electromagnetic Drive System

Figure 5A:
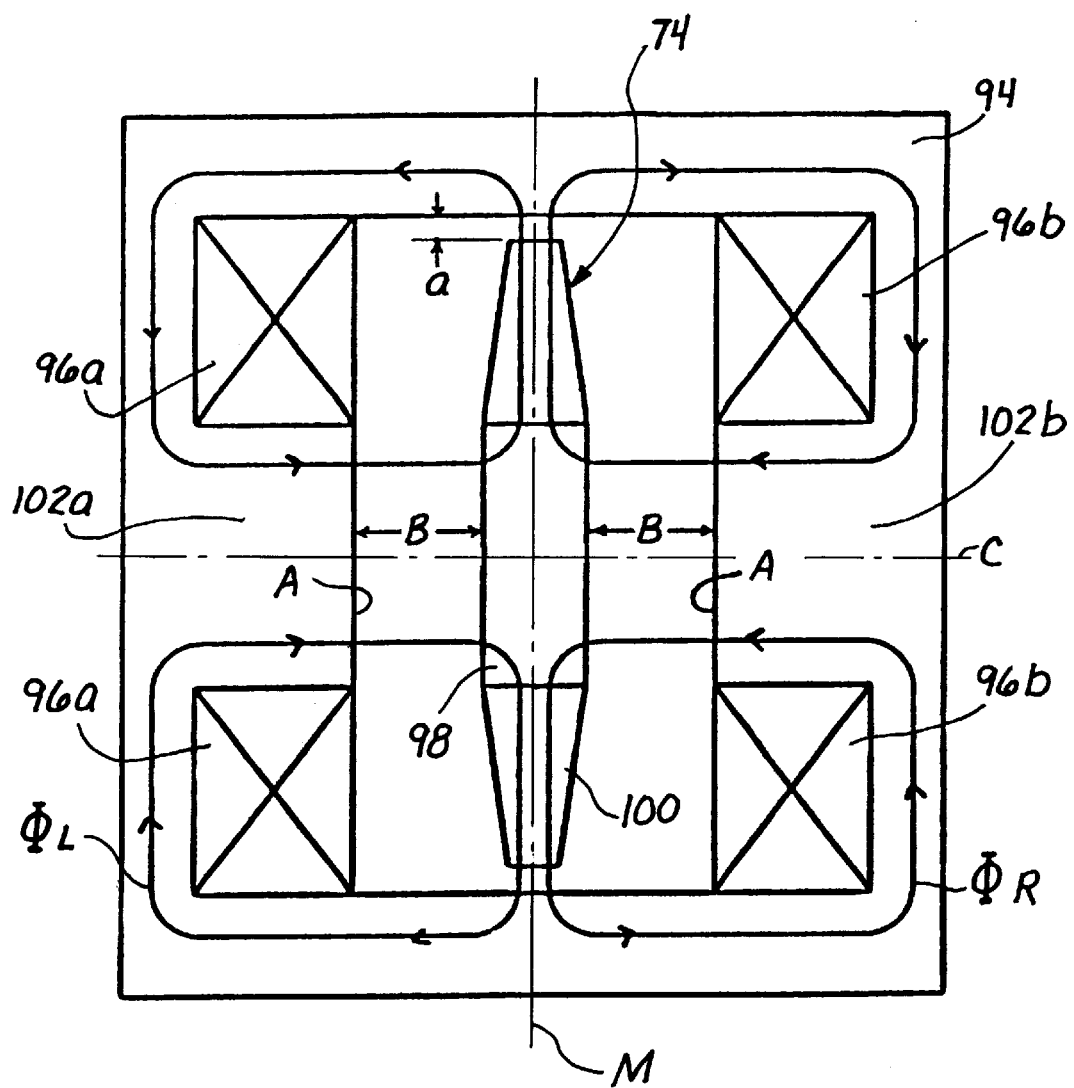
FIG. 5A is a schematic view of an exemplary drive structure of the invention, illustrating a magnetic flux path generated by a bias magnet on an armature (shown in an equilibrium position) and a coil flux path generated by a fixed electromagnetic coil.

With reference to FIG. 3 and additional reference to the schematic view of FIG. 5A, the drive system of the present invention preferably comprises a substantially cylindrical electro-magnetic structure 90; accordingly, for the purposes of this description, the electro-magnetic structure 90 has a center axis C and a midplane M. In addition to the moving plate 74 which forms an armature, exemplary electromagnetic structure 90 generally includes an outer frame 94 in which is mounted a pair of electrically-conductive coils 96, including a first or left coil 96a and a second or right coil 96b. Exemplary plate 74 functions as an armature and thus has a magnetically permeable portion 98 in a radially central region and a surrounding bias magnet 100. The exemplary bias magnet 100 is a permanent magnet which is radially polarized, and the frame 94 includes a magnetically permeable portion situated so as to provide a magnetic flux path $\Phi_b$. The magnetic flux path $\Phi_b$ tends to create an instability of the plate 74 in a central position between the two variable-volume chambers 70, so that the plate is biased toward one or the other variable-volume chamber upon a slight displacement in that direction.

Figure 5B:
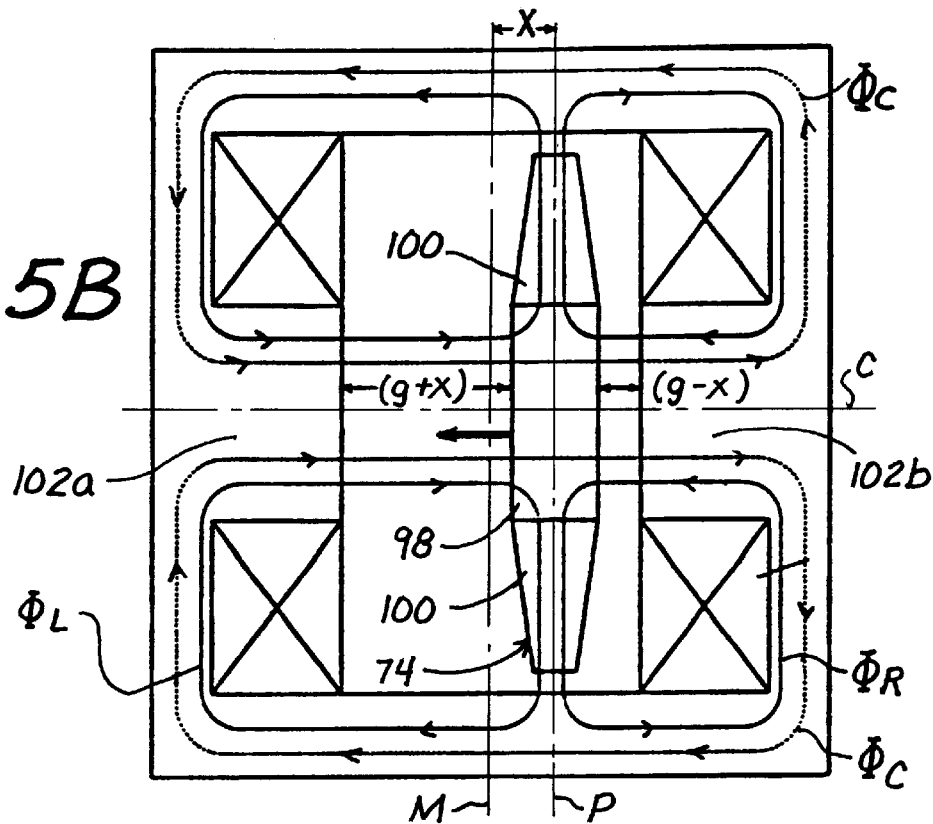
FIG. 5B is a view similar to that of FIG. 5A, showing the armature displaced to the right and being driven to the left.
Figure 5C:
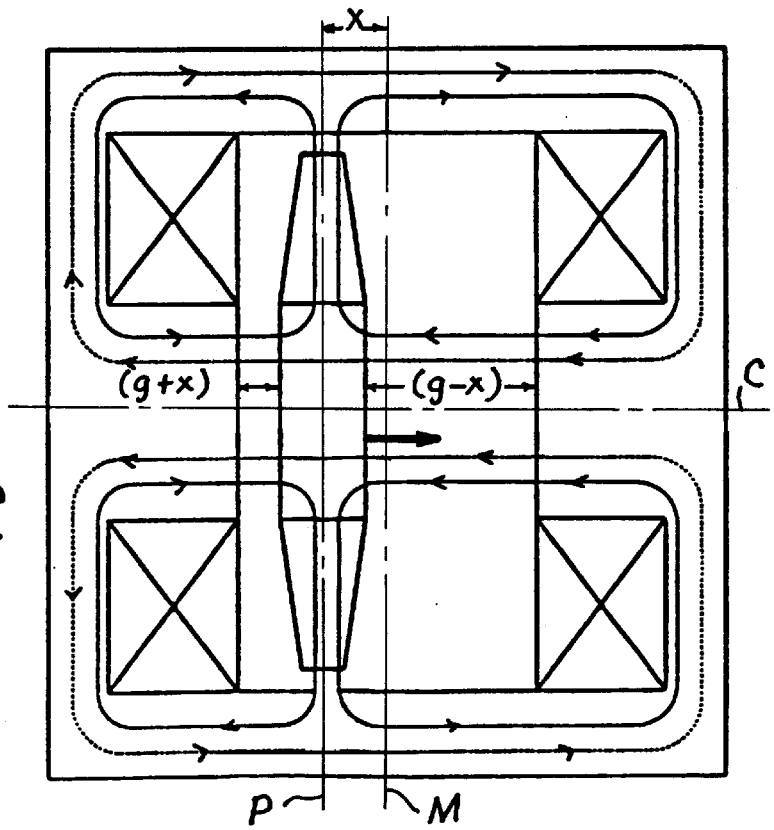
FIG. 5C is a view similar to that of FIG. 5A, showing the armature displaced to the left and being driven to the right.

As shown in FIG. 3, the coils 96, which may be configured as annular rings, are disposed in a spaced relationship within the frame 94 on opposite axial sides of the plate 74. The coils 96a and 96b are connected electrically in series and, when actuated, generate a magnetic flux defining a pair of poles 102, including a first or left pole 102a and a second or right pole 102b. The polarity of the electric circuit through the coils 96 determines the magnetic flux direction as shown in FIGS. 5B and 5C and, thus, the physical influence on the armature 98 on the plate 74.

The plate 74 is disposed within the frame 94 such that the armature 98 is positioned between the poles 102 and the bias magnet 100 is positioned between the coils 96. When the armature 98 is centered between the poles 102 at the midplane M, a gap g is defined on either side of the armature, as shown in FIG. 5A. In addition, an annular gap a having a substantially constant radial dimension is defined between the radially outermost surface of the plate 74 and an inner surface of the frame 94.

With reference to FIG. 3, each of the poles 102 defines an inwardly facing surface 103, generally within the annular coils 96, disposed normal to the central axis C and facing the armature 98. The frame 94 includes a pair of centrally-located, outwardly-facing cylindrical cavities 104 having tapered floors 105 so that the poles 102 comprise annular regions 106 that transition along the tapered floors 105 to the area of the inwardly facing surfaces 103. In this manner, the overall mass of the device is reduced which helps facilitate patient acceptability and comfort.

The exemplary pump 28 may also include pairs of springs 112a and 112b radially disposed about a periphery of the chamber 70 and each disposed to provide a compressive bias between the plate 74 and one side of the frame 94. Only one pair of springs 112 is shown in the drawings because of the offset cross-section taken along line 3—3 of FIG. 2. Although exemplary springs 112 are shown as helical compression springs, any spring configuration that resists displacement of the armature 98 away from the midplane M may be used, for example, leaf springs, one large spring on each side of the chambers 70 such as a large diameter coil spring, and the elasticity of the chambers 70 themselves. Desirably, the springs exert axisymmetric forces on both sides of the plate 74 tending to center the plate at the midpoint M. Accordingly, the combined forces of the springs 112, and to a lesser extent the forces exerted by the elasticity of walls of the sacs 72, oppose the force of the bias magnet 100 and tend to maintain the plate 74 substantially equidistant from the poles 102 when the coils 96 are not activated.

Electromagnetic Drive System Function

Radially polarized bias magnet 100 generates bias flux $\Phi_b$ that follows a closed magnetic circuit including the frame 94, a respective one of the poles 102, a respective one of the gaps g, and the armature 98. Advantageously, electromagnetic flux $\Phi_c$ generated by the coils 96 does not travel a path through the bias magnet 100, but instead traverses around the outside of the frame 94 and through the poles 102, gap g, and armature 98; accordingly, the bias flux $\Phi_b$ remains substantially constant and predictable. As the bias flux $\Phi_b$ is substantially constant, the bias magnet 100 is not subject to depolarization, which is discussed in more detail below.

The armature 98 of exemplary plate 74 moves either right as shown in FIG. 5B or left as shown in FIG. 5C by a distance indicated as x representing a displacement of a midplane P of the plate 74 from midplane M of the electromagnetic structure 90. With particular reference to FIG. 5B, when electrically activated, the coils 96 generate coil flux $\Phi_c$ which follows a path including the frame 94, one of the poles 102a or 102b, one of the gaps (either [g+x] or [g−x]), the armature 98, the other gap, the other pole, and the frame.

As discussed in detail below, exemplary electromagnetic structure 90 is configured so that:

(a) the coil flux $\Phi_c$ follows a substantially closed path to make efficient use of the bias magnet 100;

(b) the total bias flux $\Phi_b$ is substantially constant to eliminate depolarization of the bias magnet 100 which generates the bias flux;

(c) a relatively low magnetic field intensity (H) over a relatively large area A of the poles 102 significantly reduces the need for high-precision components; and (d) energy conversion is linear to simplify optimization and control.

Figure 6:
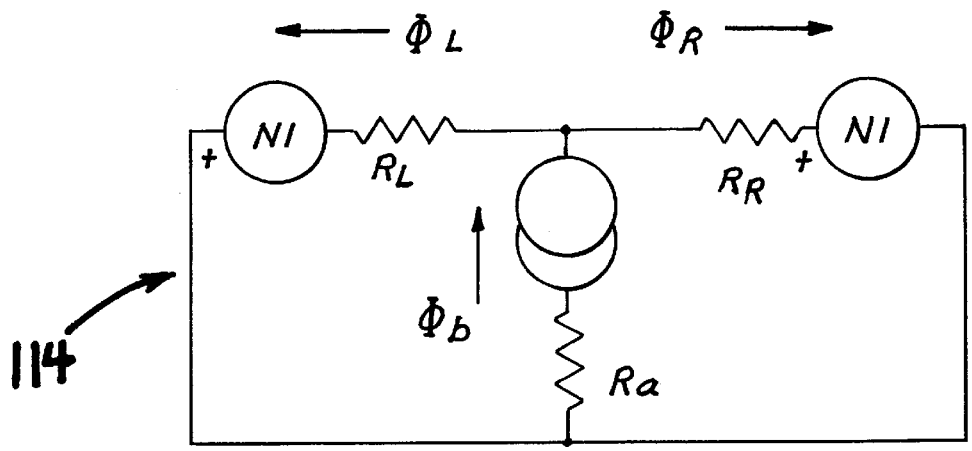
FIG. 6 is a circuit diagram of a magnetostatic equivalent circuit for the exemplary drive structure of the present invention.

With reference to FIG. 6, a magnetostatic equivalent circuit 114 of the electro-magnetic structure 90 shown in FIG. 5B is illustrated. The magnetostatic circuit 114 includes circuit elements equivalent to components of the electromagnetic structure 90: left coil 96a', right coil 96b', bias magnet 100', left reluctance $R_L$, right reluctance $R_R$, annular gap reluctance $R_a$, left flux$\Phi_L$, right flux$\Phi_R$, and bias flux$\Phi_b$. Each of the coils 96' is represented by a number of turns N and current I. Exemplary electro-magnetic structure 90 is configured so that the maximum values of the left and right fluxes $\Phi_L$ or $\Phi_R$ traversing between the armature 98 and the poles 102 of FIG. 5B (and the connected parts of electromagnetic structure 90) are below the magnetic saturation level of the armature 98 and poles 102; accordingly, the magnetostatic equivalent circuit 114 is linear. Also, exemplary electromagnetic structure 90 is preferentially configured so that fringing magnetic fields located around the poles 102 and the annular gap a are insignificant; therefore, the reluctances $R_L$ and $R_R$ are substantially proportional to the gaps, such as:

$$R_L=(g+x)/A \quad (1a)$$

$$R_R=(g-x)/A \quad (1b)$$

To assure this proportionality, the poles 102 preferably have a relatively large area A. Accordingly, the magnetic flux density (B) is preferably on the order of 0.5 tesla (T) for an exemplary blood pump embodiment. A magnetic flux density of this magnitude is significantly less than the magnetic flux density saturation ($B_{SAT}$) of core material used in the armature 98 and the poles 102. Therefore, exemplary plate 74 may have a hollow armature 98 (as shown in FIG. 3) to reduce the size and weight of the overall electromagnetic structure 90.

As the system is linear, the superposition principle applies. Accordingly, the bias fluxes $\Phi_L$ and $\Phi_R$ and the coil flux$\Phi_C$ may be calculated separately. The left and right bias fluxes $\Phi_L$ and $\Phi_R$ are calculated by solving the magnetostatic equivalent circuit 114 in FIG. 6 with no coil current (that is, NI=0):

$$\Phi_L=\Phi_b(g-x)/2g \quad (2a)$$

$$\Phi_R=\Phi_b(g+x)/2g \quad (2b)$$

The magnetic energies in the left and right gaps can then be calculated and combined to give the total bias energy ($W_b$) and force ($F_b$) due to the bias magnet 100 for the case when the coil current is zero (i.e., I=0):

$$W_b=\Phi_b^2(g^2-x^2)/4\mu_o gA \quad (3)$$

$$F_b=\partial W/\partial x=-\Phi_b^2 x/4\mu_o gA$$

(where $\mu_o$ is the permeability of free space, or $4\pi*10^{-7}$ in SI units) (4)

Accordingly, as the armature 98 moves to the right (i.e., toward right pole 102b), the bias flux$\Phi_b$ shifts from left to right, with the total flux$\Phi_b$ remaining constant. As energy W and force F vary with $\Phi^2$, the shift in the bias force $F_b$ is marked. This phenomenon is illustrated in FIG. 5B. The shift in the bias force $F_b$ constitutes a negative spring (k) that can be used to balance the elasticity of the chambers 70, which will be discuss in detail below. As shown in Equation 3, the bias energy $W_b$ is independent of coil current.

Exemplary bias magnet 100 is preferably made from a material having a high energy density and a low marginal permeability, for example, rare earth material such as samarium cobalt (SmCo) or neodymium iron (NdFe). Accordingly, the bias magnet 100 as described above and as shown in circuit 114 of FIG. 6 is a source of flux. Therefore, the bias flux$\Phi_b$ is constant in the bias magnet 100, and all of the flux$\Phi_C$ generated by the coils 96 traverses the loop shown by the dashed lines in FIG. 5B, including the frame 94, the left pole 102a, the left gap (g+x), the armature 98, the right gap (g-x), the right pole 96b, and the frame 94. Accordingly, the coils 96 produce a magnetic field intensity as:

$$H_C=2NI/[(g+x)+(g-x)]=NI/g \quad (5)$$

and a magnetic flux as:

$$\Phi_C=AB_C=\mu_o ANI/g \quad (6)$$

Energy of the left and right gaps may then be determined by using Equations 3 and 6 and adding the bias flux$\Phi_b$ and the coil flux$\Phi_C$ contributions in the gaps g. The total energy $W_T$ has the bias component $W_b$ represented by Equation 3 and the following coil self-inductance energy $W_{CC}$:

$$W_{CC}=\Phi_C^2 g/\mu_o A \quad (7)$$

The product energy terms, that is, terms containing ($\Phi_C$ and $\Phi_L$) or ($\Phi_C$ and $\Phi_R$), add to zero. This is a necessary consequence of the magnetic linearity. Accordingly, there is no energy component dependent on the product of the two fields. In addition to having a small magnitude, the self-inductance energy $W_{CC}$ does not depend on displacement x or on flux$\Phi$, which is also required by the linearity assumption, such that the self-inductance energy $W_{CC}$ does not contribute to mechanical force. As such, movement of the armature 98 merely shifts a portion of the gap g (i.e., displacement x) from side to side but does not change the total reluctance of the loop.

The force contributed by the coil current I is calculated from the total energies in the left and right gaps (holding the left and right bias fluxes $\Phi_L$ and $\Phi_R$ constant):

$$F_C=\partial W_{CB}/\partial X=-NI\Phi/2g \quad (8)$$

The coil force $F_C$ is independent of displacement x and area A and is linear in flux d). Accordingly, the following total force $F_T$ equation results from the bias force $F_b$ and the coil force $F_C$ respectively represented by Equations 4 and 8:

$$F_T=F_b+F_C=-\Phi_T^2 X/4\mu_o gA-NI\Phi/2g \quad (9)$$

It can be seen from Equation 9 that the effect of the coil current I is to move bias energy $W_b$ side to side without affecting total energy $W_T$ except for the small self-inductance energy $W_{CC}$.

Equation 9 enables wide design latitude through varying the flux$\Phi$ and the area A of the poles 102 as the area A does not contribute to the coil force $F_C$. For example, it is desirable for the value of the flux$\Phi$ to be large as flux directly determines the coil force $F_C$ generated by a given coil current I. For a given coil geometry, force F is proportional to the product of number of turns N and coil current I (that is, F NI), and power dissipation $P_{Diss}$ is as follows:

$$P_{Diss}=I^2R\,(NI)^2 \quad (10)$$

Accordingly, efficiency may be improved by using a high flux$\Phi$ and a modest NI. To prevent the large flux$\Phi$ from developing too much bias force $F_b$ (which is balanced by the elasticity of the chambers 70 and/or springs 112), the poles 102 preferably have a relatively large area A. A large pole area A, in turn, implies a low value of magnetic flux density B; accordingly, the effect of fringing fields is minimized or substantially eliminated.

Electromagnetic Drive System—forces

Figure 7:
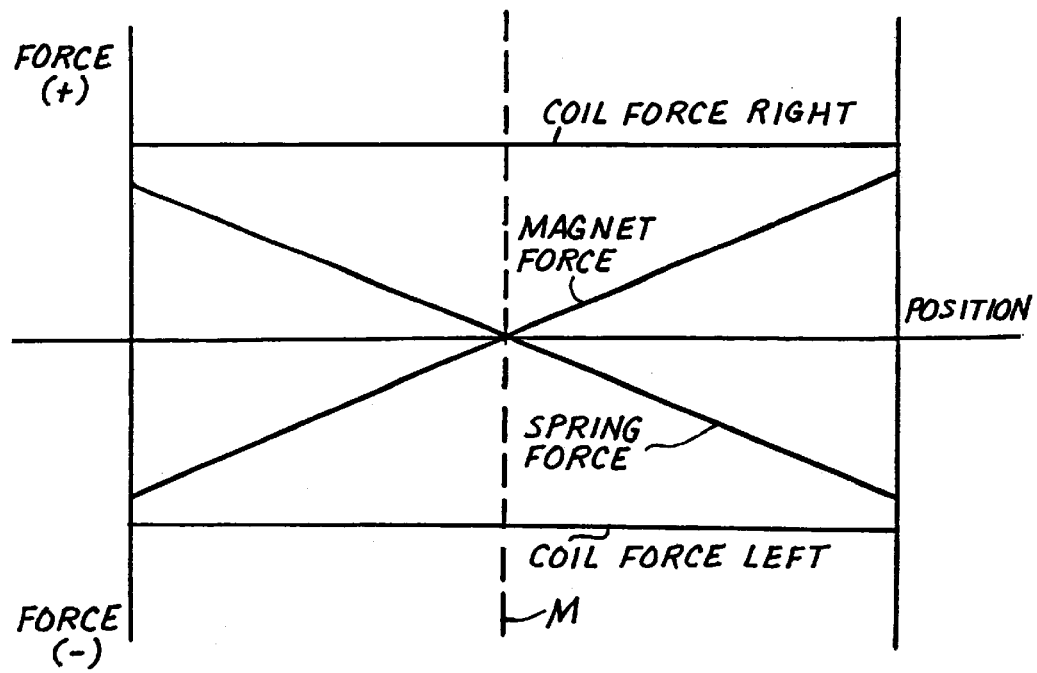
FIG. 7 is a graph showing various force components of the drive structure superimposed along a position axis.

FIG. 7 illustrates the forces exerted on the plate 74 by the various components of the electromagnetic structure 90. The horizontal axis corresponds to the centerline C of the pump 28, with the midplane M shown, and the vertical axis represents forces on the plate 74, with a positive force representing a force on the plate 74 to the right using the conventions established herein. First, the force exerted by the bias magnet 100 is seen as a positive slope illustrating its unstable nature tending to displace the plate 74 away from the midplane M in all positions. Of course, the force created by the bias magnet 100 flux is idealized, and there would normally be some fringing loss. Secondly, the preferably equal and opposite force exerted on the plate 74 by the spring 112 (and perhaps in conjunction with the sac 72) is seen as a negative slope, indicating that the spring force would tend to center the plate 74. Finally, there are two different forces associated with the coils 96. A force tending to displace the plate 74 to the right is seen at the top of the graph and represents the coil current flow seen in FIG. 5B. In like manner, a force tending to displace the plate 74 to the left is seen at the bottom of the graph and represents the coil current flow seen in FIG. 5C.

In the exemplary embodiment shown in FIG. 3, the springs 112 provide all or a substantial portion of the force offsetting that of the bias magnet 100. One of the advantages of incorporating the springs 112 into the embodiment of the pump 28 shown in the drawings is that the force characteristics of the springs 112 is more predictable and stable than that produced by the elastomeric material composing the chambers 70. Alternatively, the elasticity of the chambers 70 may partly or completely offsets the force produced by the bias magnet 100, and no springs would be used. In such a configuration, however, the thickness of the sacs 72 would have to be increased beyond what is currently preferred for stress considerations.

The electro-magnetic structure 90 functions in a way as to reduce the power needed for displacing the plate 74 and substantially eliminate the possibility of depolarizing the magnet 100. More particularly, with reference to FIGS. 5B and 5C, the magnetic flux$\Phi_b$ travels a radially outward path and then splits to travel around the frame and back to the plate 74 essentially along the centerline C. In contrast, the coil flux$\Phi_c$ travels around a larger path, always going in the same direction along the radially outermost portion of the frame 94 for any one current flow direction. Therefore, the magnetic flux$\Phi_b$ opposes the coil flux$\Phi_c$ in the region of the frame in which they travel in opposite directions, and supplements the coil flux$\Phi_c$ in the region of the frame in which they travel in the same direction. In FIG. 5B, for example, the magnetic flux$\Phi_b$ opposes the coil flux$\Phi_c$ on the right side of the diagram and supplements the coil flux$\Phi_c$ on the left side.

Looking at the structure in another way, and as illustrated in FIG. 7, the force exerted on the plate 74 by the bias magnet 100 and the force by the spring 112 cancel each other to leave the constant force generated by the coils. Therefore, the force and pump pressure vary directly with the product NI regardless of the displacement x of the armature 98; accordingly, the control of the pump is simplified. In addition, as both inductance and the effects of inertia are negligible in the relevant time domain, control of the pump 28 is further simplified. For example, when the coils 96 are not energized, the pressures in the chambers 70 equalize by means of the inlet of blood through the inlet conduit. The difference between inlet and outlet pressures is proportional to coil current I when the pump 28 is simultaneously filling and ejecting the chambers 70, which is any time the plate 74 is moving.

Ventricular Assist System—Coordination with Heart

Referencing FIGS. 8A–8E and taking the foregoing into consideration, it is advantageous from an energy point of view to accept and pump blood ejected by the assisted ventricle during systole (i.e., ventricular contraction) as rapidly as is consistent with fluid flow considerations, and to stop pumping during diastole (i.e., ventricular dilation). In this discussion systole and diastole correspond to inflow to and outflow from the ventricular assist system 22, respectively, in the context of either left or right ventricular assist.

Figure 8:
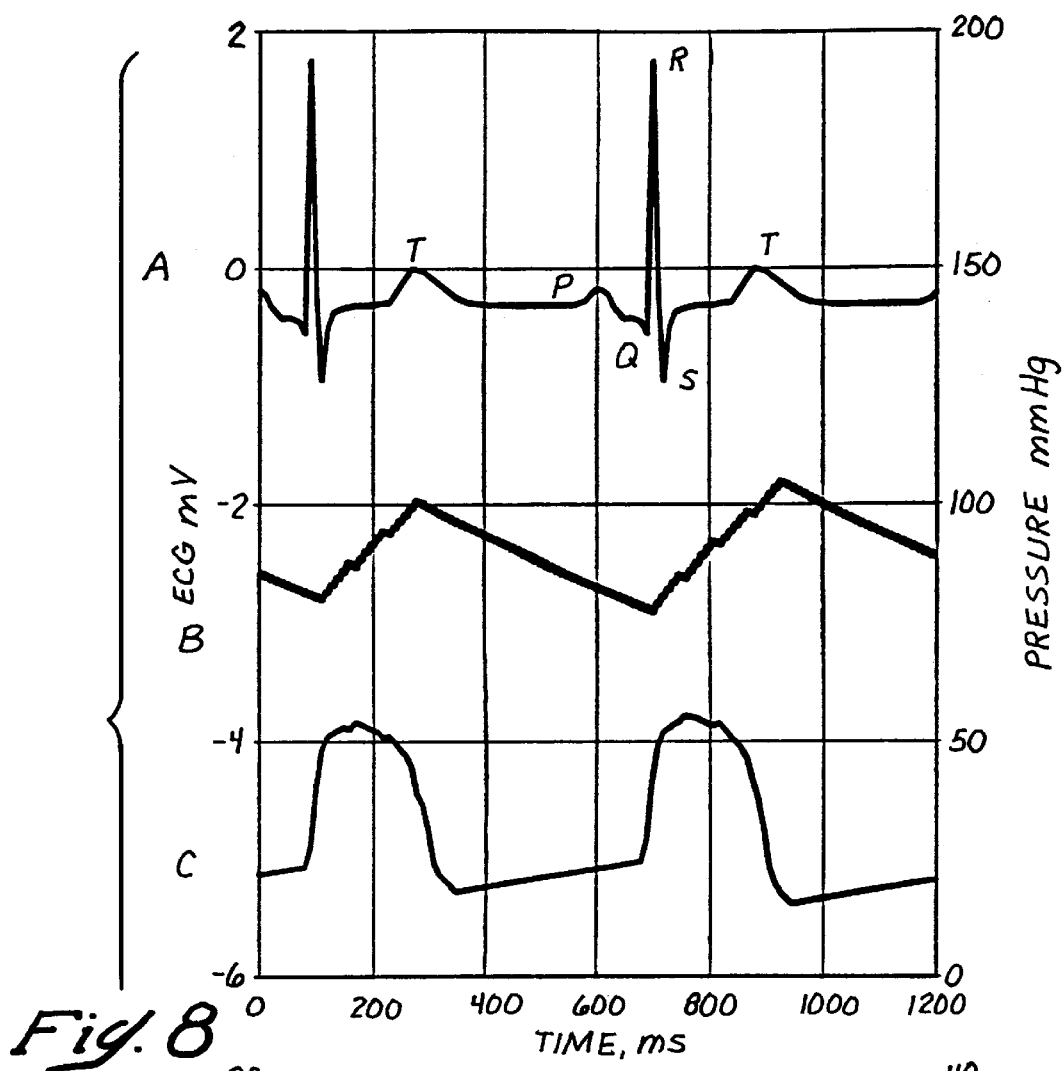
FIGS. 8A to 8E are diagrammatic views illustrating phasing relationships among (A) an electrocardiogram signal, (B) left-ventricular pressure, (C) aortic pressure, (D) armature position, and (E) pump outlet.
Figure 8:
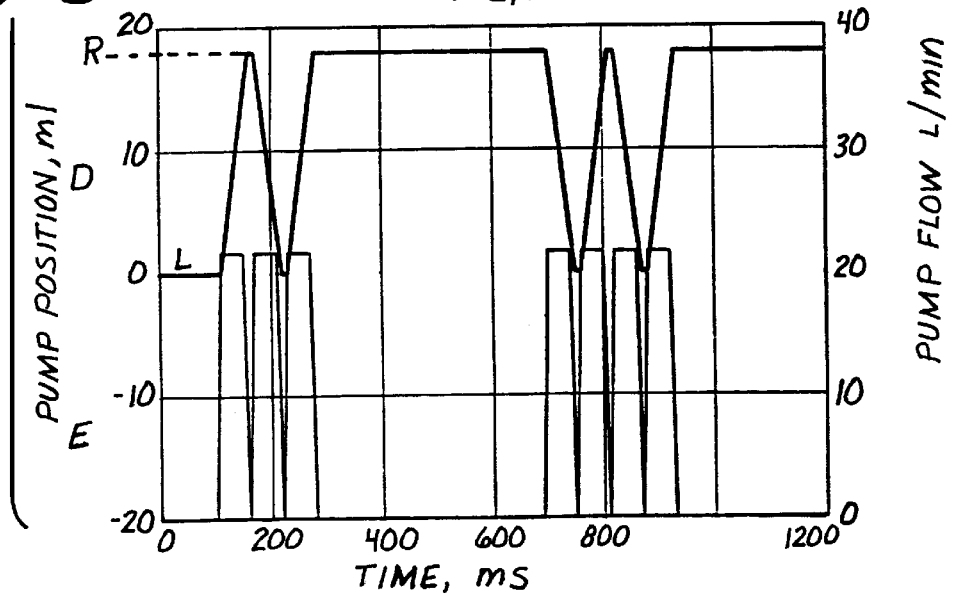

As shown in FIG. 8A, an exemplary electrocardiogram (ECG) records the changing potentials of the electrical field imparted by the heart. To briefly explain the cycle of systole and diastole, the ECG signal shown in FIG. 8A illustrates a series of points representing various muscle contractions within the heart. Generally, blood is received in the left ventricle and it fills during the T-Q period. Then, during the period Q-T, the left ventricle contracts and expels blood into the aorta. Accordingly, the pressure diagram in FIG. 8C shows the left ventricular pressure rapidly increasing during the spike indicated at R on the ECG signal. For the purposes of this description, ventricular systole may be considered as occurring between the R and T points on the ECG wave.

FIGS. 8D and 8E illustrate and exemplary movement of the actuator 74 in and outflow pressure of the ventricular assist system 22, respectively, in correlation with the signals shown above in FIGS. 8A–C. FIG. 8D illustrates the position, from left (L) to right (R), of the plate 74. When the heart enters systole (e.g., at the beginning of the QRS complex of the ECG), the controller 40 activates the coils 96 to move the plate 74 to the right (R) to accept blood from the left ventricle into one of the chambers 70 (for example, the left chamber 70a as shown in FIG. 4A). As the chambers 70 preferably have a relatively small capacity or volume, for example, 20 ml, compared to the 80 ml ejection volume of the left ventricle, the controller 40 repeatedly activates the coils 96 to move the plate 74 back and forth during systole to accept and pump a substantial portion or all of the blood entering the left ventricle from the left atrium.

For example, referencing FIG. 8E, if each chamber 70 has a volume of about 20 ml, then each stroke of the plate 74 pumps about 20 ml. Accordingly, to accommodate the typical 80 ml capacity of the left ventricle, the controller 40 may initiate four strokes of the plate 74, thereby pumping about 80 ml of blood total during systole. If the time required to complete each stroke (i.e., stroke time) is on the order of about 40 msec, then a volume of about 80 ml may be pumped in a typical 160 msec ejection time. Given this exemplary stroke cycle, the pump 28 of the invention may have a weight of about 500 grams and may pump about 6 liters/minute into a typical systemic pressure of about 100 mm Hg while consuming about 5.5 watts of energy. This energy consumption is significantly lower than conventional ventricular assist devices.

The sequence of strokes of the actuator 74 shown on the right side of FIG. 8D results in four side-by-side pressure pulses as seen on the right in FIG. 8E. These pressure pulses are slightly trapezoidal in shape given the slight lag time between movement of the actuator 74 and pressure change. However, given the extremely short time duration for each stroke of the actuator, pressure pulses produced a nearly constant outflow of blood from the ventricular assist system 22. Indeed, if the actuator 74 continued to move back and forth without stopping, the outflow of the ventricular assist system 22 would be approximately continuous. As it is, a short duration of approximately continuous flow of blood is generated at the appropriate time to assist the left ventricle in perfusing the circulatory system of the patient (or for an RVAD, to assist the right ventricle in perfusing the pulmonary system of the patient).

The output from the system is represented by the aortic pressure shown in FIG. 8B. As can be seen, the aortic pressure lags slightly behind ventricular pressure and is not quite as pronounced in terms of peaks. FIG. 8B shows small discontinuities or steps in the rise of the aortic pressure, which correspond to the closely spaced pulses from the ventricular assist system 22.

Control of Ventricular Assist System

If the heart is performing at below capacity, the magnitude of the ECG or pressure signals may not be as large is normal, but the timing of the various modes of operation will remain essentially the same. Therefore, the signals sensed by either ECG, pressure sensors, flow sensor, or other such information gathering device, can be used to stimulate the ventricular assist device of the present invention.

Because the ECG records electric impulses generated by the muscles of the heart, this provides an indication of the frequency of the heart beat, and relative timing of the systole and diastole phases. This information may then be used to control the ventricular assist device of the present invention, as will be described below. It will be understood, however, that various other means for sensing changes within the heart representing the "normal" or reference beat frequency are known.

The ECG provides an indirect indication of the relative amplitude of the pressure and flow outputs, but other more direct measurements can be taken and should be used alone or in conjunction with the ECG signal in the control loop of the present invention. For example, with reference to FIG. 2, exemplary pumping system 20 may also include one or more sensors for sensing the pressure in the assisted ventricle of the heart H of the patient. In this regard, a preload sensor 130 is preferably located upstream of the pump 28 on the bifurcation 50. The sensor 130 is in communication with the controller 40 by, for example, an electrical lead (not shown) incorporated in the cable 38. The controller 40 may utilize pressure information provided by the sensor 130 to determine when to activate the coils 96 to pump blood.

In a preferred embodiment, the ventricular pressure is monitored by the sensor 130 and the coils 96 are activated when that sensed pressure exceeds a preset threshold pressure. The coils 96 remain activated until the sensed pressure decreases to below the threshold pressure. This rise and fall of ventricular pressure theoretically corresponds to the systolic phase, and so the entire ejection volume of the ventricle enters and is propelled by the ventricular assist system 22. In a preferred mode of operation, the coils 96 are activated to maintain the ventricular pressure monitored by the sensor 130 within a preset range.

The number of strokes of the actuator 74 during each systolic pumping phase is determined by the volumetric outflow of each of the variable-volume chambers 70. That is, the outflow of the ventricular assist system 22 during any one systolic phase is preferably about the normal outflow volume of the assisted ventricle. Therefore, if the volume of the chambers 70 is exactly half of that of the assisted ventricle, and given normal outflow of the ventricle, the actuator 74 will only need to move back and forth once (one cycle, two strokes) to generate a total volumetric outflow equal to the assisted ventricle volume. Likewise, if the chamber volume is one-quarter the volume of the assisted ventricle, actuator 74 will go through 2 cycles, or four strokes, as seen on the right of FIG. 8D. To generalize, the volume of the chambers 70 is desirably a fraction of the volume of the assisted ventricle, with a maximum of half the volume of the assisted ventricle. When the total ventricular ejection has been pumped, the preload or inlet pressure drops below the threshold value and the device stops pumping.

Of course, the ratio of volume of the chambers 70 to the actual volumetric output of the assisted ventricle will not be a round fraction, but given an estimate of the ventricular output one can select the chamber volume so that the device will function optimally. That is, the volume of the chambers 70 is selected based on an estimate of the ventricular output, and understanding of an optimum operating speed of the device. Broadly stated, the variable-volume chambers 70 preferably each have a volume which is within the range of ⅛ to ½ of the volumetric output of the assisted ventricle. Theoretically, the chambers 70 could be made smaller, which would accordingly make the entire device smaller, but would also increase the speed of operation. Eventually, flow and valve wear considerations limit the chamber size. A preferred range of chamber volume is between about ⅙ and ⅓ of the assisted ventricle volume, with the most preferred volume being about ¼ of the assisted ventricle volume. With this preferred volume, and given normal outflow of the ventricle, each operation during the systolic pumping phase requires four strokes, or two cycles, of the actuator 74.

Conceivably, a series of devices manufactured in accordance with present invention and having different chamber volumes can be made available and selected based on a predicted assisted ventricle volume. It should also be apparent that a device with relatively small chamber volumes, such as ⅛ of the assisted ventricle volume, can be used in a wide range of patients at differing speeds, for example, to accommodate a wide range of ventricular outflows. As will be appreciated by those of skill the art, the range of operating modes of the present invention greatly enhances the ability of the medical personnel to customize the ventricular assist system.

Diastolic Operation

In a preferred mode of operation, as seen in FIGS. 8D and 8E, the ventricular assist system 22 is actuated during the systolic phase, and rests during the diastolic phase. Alternatively, the ventricular assist system 22 may be actuated one more times during the diastolic phase to reduce the possibility of stasis within the respective inflow and outflow conduits and variable-volume chambers 70. One exemplary mode of operation is to displace the actuator 74 one stroke about halfway through the diastolic phase, although other possibilities during the diastolic phase include a relatively consistent and slow movement of the actuator 74, or relatively rapid movement spaced out at a slower frequency than the actuation frequency during the systolic phase. Another possibility is to operate the system 22 at a first frequency during the systolic phase (the duration of which is based on the sensed inflow pressure), and at a second lower frequency during the diastolic phase, with intermediate modes of frequency ramp-up and ramp-down to avoid abrupt changes therebetween. In general, however, the present system operates during the systolic pumping phase until the ventricular pressure falls below the threshold level, and does not operate or else operates only intermittently during the diastolic phase.

Series—Displacement VAD

In addition to the parallel pumping relationship of the chambers 70 shown in FIG. 4, the pump 28 may be configured in accordance with the alternative ventricular assist system 22' shown in FIGS. 9 and 10A–10F in which the chambers 70 are connected in series. Many of the elements are common to the first embodiment and will thus be numbered the same. As before, the flexible inlet segment 30 of the inlet conduit 24 connects to, for example, the left ventricle LV of the heart H (see FIG. 1) and the flexible outlet segment 32 of the outlet conduit 26 connects to, for example, the aorta AO. In this embodiment, the flexible inlet segment 30 is only connected to the inlet port 132 of one of the chambers (such as the left chamber 70a), and the flexible outlet segment 32 is only connected to the outlet port 133 of the other chamber (such as the right chamber 70b).

Figure 9:
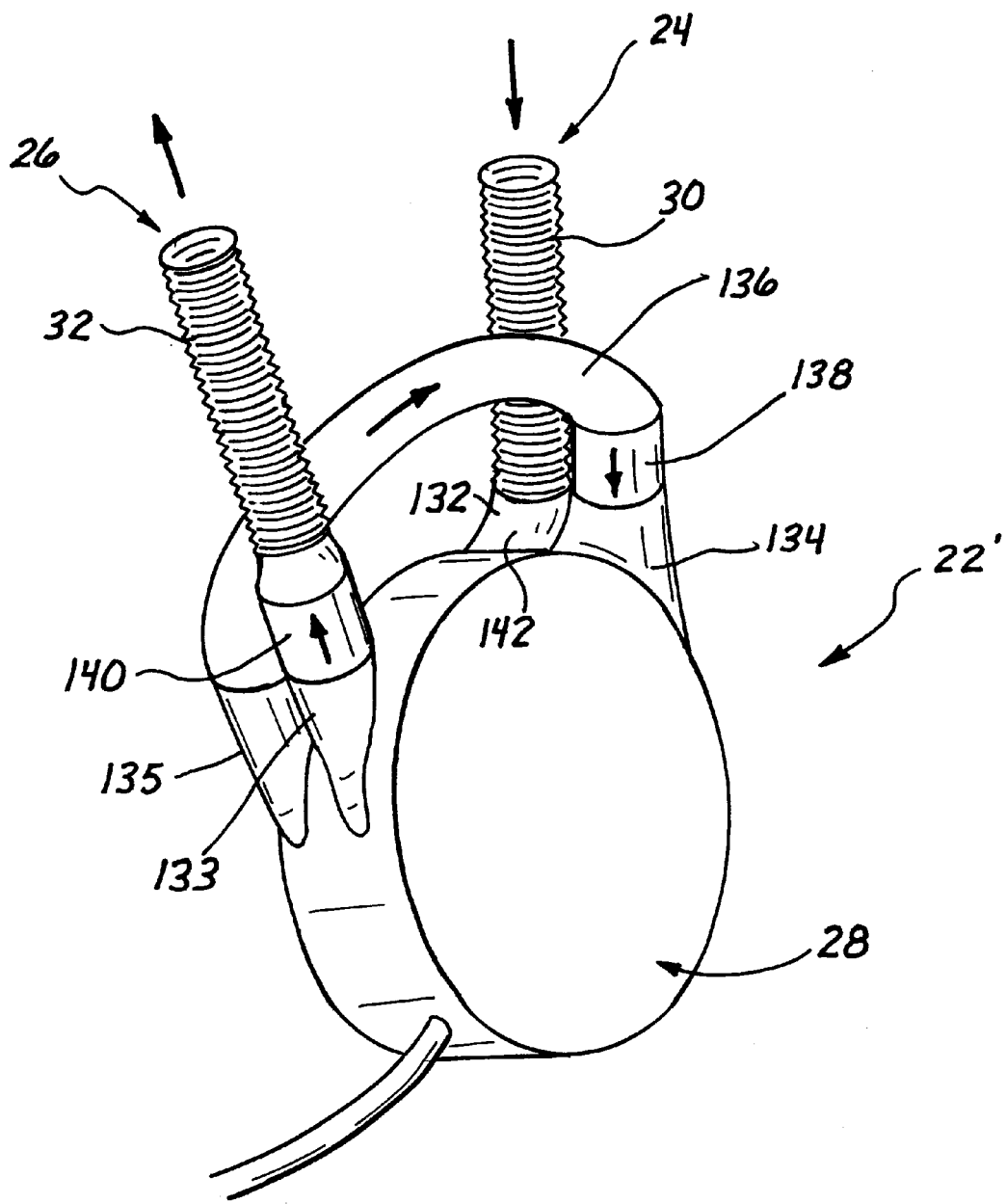
FIG. 9 perspective view of an alternative blood pump of the present invention in which variable-volume chambers operate in series.

According to the embodiment shown in FIG. 9, a transfer conduit 136 is connected between the outlet port 135 of the chamber connected to the flexible inlet segment 30 (the left chamber 70a) and to the inlet port 134 of the chamber connected to the flexible outlet segment 32 (the right chamber 70b). In addition, a pair of valves are provided, including an inlet valve 138 disposed at the inlet port 134 of the chamber connected to the outlet conduit 26 and an outlet valve 140 disposed at the outlet port 133 of the chamber connected to the outlet conduit 26.

In accordance with the series flow blood pump 28 exemplified in FIG. 9, blood from the left ventricle is initially pumped to the left chamber 70a in the inlet conduit 24. The coils 96 are activated to move the plate 74 to the right as shown by the arrow in FIG. 10A, thereby ejecting blood received within the right chamber 70b through the outlet port 133 and the outlet valve 140 and into the flexible outlet segment 32 for delivery to the aorta. During this ejection stroke of the plate 74, the inlet valve 138 prevents blood from entering the transfer conduit 136. In addition, the left chamber 70a is expanded, thereby drawing oxygenated blood through the inlet conduit 24 from the left ventricle LV into the left chamber as shown in FIG. 10B. At the end of the ejection stroke as shown in FIG. 10C with the plate 74 positioned to the right, the left chamber 70a is filled with oxygenated blood from the left ventricle, and the right chamber 70b is compressed to a minimum volume.

The coils 96 are then activated to move the plate 74 to the left as shown by the arrows in FIGS. 10D and 10E, thereby drawing blood from the left chamber 70a into the right chamber 70b via the transfer conduit 136. The outlet valve 140 prevents blood in the aorta or the outlet conduit 26 from being drawing back into the right chamber 70b. In addition to left ventricular pressure, the low pressure within the right chamber 70b caused by the expansion of the chamber ensures that blood within the left chamber 70a enters the right chamber 70b and is not ejected back into the inlet conduit 24. If desired, an additional valve may be disposed at the inlet port 132 of the left chamber 70a to also prevent blood from entering the inlet conduit 24. At the end of the transfer stroke as shown in FIG. 10F with the plate 74 positioned to the left, the right chamber 70b is filled with oxygenated blood from the left ventricle, and the left chamber 70a is compressed to a minimum volume. The ejection stroke illustrated in FIGS. 10A–10C and the transfer stroke illustrated in FIGS. 10D–10F may repeated in accordance exemplary methodology of the invention described above.

The series flow generated by the ventricular assist system 22' may be used in many of the same modes of operation as described above, although the continuity of the flow is not available. Control of the system 22' may be based on the input pressure sensed at sensor 142 as described above. One advantage of the ventricular assist system 22' is the reduction of the number of valves needed, from four to two. This in turn reduces the cost of the device.

Advantages of Present System

As will now be apparent to those of skill in the art, the present ventricular assist system 22 provides regularly spaced and sustained pulses of blood to the circulatory system of the patient using a pulsatile pump. This represents a hybrid between existing pulsatile flow pumps, and rotary type pumps. Although the present system enjoys the advantages of both types of pumps, it suffers none of their primary disadvantages. In particular, the superior hemocompatibility of pulsatile flow pumps is combined with the smaller size and lower energy requirements of rotary type pumps. In addition, the system eliminates the need for a vent or compliance chamber, and is thus fully implantable if used with an inductive power transmission system. Further, the present invention maintains a unidirectional pathway therethrough so that in the event of stoppage or failure, regurgitation from the natural circulatory system into the outlet of the device is precluded. Finally, operation flexibility inherent in the design greatly enhances the ability of medical personnel to react to changing physiological conditions of the patient. That is, as the rate of the heart beat speeds and slows, and the blood volume requirements fluctuate, the present system is able to adapt and therefore more effectively support the patient to full recovery.

To facilitate implantability, it is preferable to minimize the overall size of the blood pump 28. As such, and as indicated in FIG. 2, according to an exemplary embodiment of the invention the substantially cylindrical pump 28 has a diameter D in general of less than 100 millimeters (mm) and preferably less than about 70 mm. Additionally, the pump 28 has a width w in general of less than about 60 mm and preferably less than about 50 mm. Accordingly, such a small size enables the pump 28 to be implanted in a wide variety of patients, even those patients of smaller stature.

In addition, the pump is reduced in weight from conventional pulsatile pumps by about half. The present invention desirably weighs about 0.5 kilogram, which lessens the burden on the patient after implantation.

Conclusion

Those skilled in the art will understand that the preceding exemplary embodiments of the present invention provide the foundation for numerous alternatives and modifications thereto. For example, the pumping system 20 may be configured to assist the right ventricle or both ventricles of the heart. In addition, rather than utilizing pressure information, the controller 40 may determine when to activate the coils 96 by using the current magnitude through the coils 96. That is, as stated above, for a given coil geometry, force F on the plate 74 is proportional to the product of number of coil turns N and coil current I. The difference between inlet and outlet pressures is proportional to coil current I when the pump 28 is simultaneously filling and ejecting the chambers 70, which is any time the plate 74 is moving, and so the actual pressure difference can be derived from knowledge of pump flow characteristics. One can therefore use the magnitude of current flow in a feedback loop to signal the ventricular assist system 22 when to start and stop. Or, the input pressure can be used in conjunction with the coil current for control purposes. These and other modifications are also within the scope of the present invention.

What is claimed is:

1. A device for assisting the pumping capacity of one ventricle, comprising:

an implantable housing;

a pair of variable-volume chambers mounted in the housing, each of the chambers having an inlet port and an outlet port;

at least one ventricular outflow conduit adapted to be connected between the ventricle and the inlet ports said ventricular outflow conduit comprising a device inlet conduit branching to the two inlet ports;

and an actuator disposed to alternately contract one of the variable-volume chambers while expanding the other, and vice versa, to provide a positive displacement pump.

2. The device of claim 1, further including at least one one way valve provided in said ventricular outflow conduit to prevent upstream regurgitation from each of said variable volume chambers.

3. The device of claim 2, further including at least one device outlet conduit adapted to be connected between the outlet ports and at least one arterial vessel, and at least one one way valve provided in said outlet conduit to prevent downstream regurgitation into each of said variable volume chambers.

4. The device of claim 3, wherein the device outlet conduit comprises a single conduit branching to the two outlet ports.

5. The device of claim 1, wherein the variable-volume chambers are flexible sacs, and the actuator comprises a movable plate therebetween.

6. The device of claim 5, wherein the movable plate is free of mechanical connections to the housing and is sandwiched between opposing faces of the flexible sacs.

7. The device of claim 6, wherein the movable plate is attached to each of the flexible sacs.

8. The device of claim 5, wherein the movable plate comprises a bias magnet, and a portion of the housing is magnetically permeable so that the plate is unstable in a central position between the two flexible sacs, and is biased toward one or the other sac upon a slight displacement in that direction.

9. The device of claim 8, wherein the flexible sacs and movable plate are generally circular and axially aligned.

10. The device of claim 8, further including a spring positioned in the housing to apply a centering force to the plate.

11. The device of claim 8, wherein the actuator comprises an armature with a magnetically permeable portion, the device including electromagnetic coils situated so as to generate a coil flux path through the housing and magnetically permeable portion of the armature, and wherein the coil flux generated by the coils displaces the armatures toward one of the two flexible sacs depending on the current direction through the electromagnetic coils.

12. The device of claim 1, wherein the actuator comprises an armature with a magnetically permeable portion, the device including electromagnetic coils situated so as to generate a coil flux path through the housing and magnetically permeable portion of the armature, and wherein the coil flux generated by the coils displaces the armature toward one of the two variable-volume chambers depending on the current direction through the electromagnetic coils.

13. The device of claim 12, wherein the armature includes a bias magnet portion generating a magnetic flux, and a portion of the housing is magnetically permeable and situated so as to provide a magnetic flux path for the bias magnet, and wherein the armature is unstable in a central position between the two variable-volume chambers, and is biased toward one or the other variable-volume chamber upon a slight displacement in that direction by the magnetic flux.

14. The device of claim 13, further including a spring positioned in the housing to apply a centering force to the armature.

15. The device of claim 13, wherein the bias magnet portion is out of the coil flux path.

16. The device of claim 13, wherein the variable-volume chambers are circular flexible sacs and the actuator comprises a circular movable plate therebetween and axially aligned therewith, and wherein the movable plate is free of mechanical connections to the housing and is sandwiched between opposing faces of the flexible sacs.

17. The device of claim 16, wherein there are two of the coils, annularly shaped and disposed in axial alignment with and on opposite sides of the sandwiched plate and sacs, and wherein bias magnet portion of the armature is annular and positioned in axial alignment with and generally between the annular coils.

18. The device of claim 12, further including a controller connected to supply current to the electromagnetic coils, and an input sensor positioned in the ventricular outflow conduit and connected to provide physiological data to the controller, the controller supplying current to the coils based on the physiological data so provided.

19. A ventricular assist device, comprising: a frame;

a pair of coils including a first coil and a second coil disposed in a spaced relationship within the frame, the coils generating coil flux and defining a pair of poles including a first pole and a second pole when electrically activated;

a plate including an armature and a bias magent, the plate being disposed within the frame such that the armature is between the poles, and a gap being defined between the armature and each of the poles; and a pair of compressible chambers including a first chamber and a second chamber respectively disposed between the plate and each of the coils;

the device being configured so that the coil flux follows a path including one of the poles, one of the gaps, the armature, the other gap, and the other pole, and such that the bias magnet is substantially free of the coil flux.

20. A ventricular assist device as claimed in claim 19, wherein the bias magnet has an energy density that produces a substantially constant bias flux.

21. A ventricular assist device as claimed in claim 19, further comprising a power supply connected to the coils, and a controller connected to the power supply for selectively supplying power to the coils.

22. A ventricular assist device as claimed in claim 19, wherein the compressible chambers are flexible sacs.

23. A ventricular assist device as claimed in claim 19, further comprising:

a power supply connected to and for electrically activating the coils; and a controller connected to the power supply for controlling when the power supply activates the coils.

24. A ventricular assist device as claimed in claim 23, wherein the controller causes the coils to move the plate at a stroke time of less than about 100 msec.

25. A ventricular assist device as claimed in claim 19, wherein the frame and the plate are substantially cylindrical, and the coils are annular, all being axially aligned.

26. A ventricular assist device as claimed in claim 25, wherein the armature is centrally located in the plate, the magnet annularly surrounding the armature and being between the coils.

27. A ventricular assist device as claimed in claim 26, wherein the armature has a hollow central portion.

28. A ventricular assist device as claimed in claim 26, further comprising a magnetically permeable shoe disposed between the bias magnet and an inner surface of the frame, wherein the shoe has a narrow neck which becomes magnetically saturated as the bias magnet nears the inner surface of the frame.

29. A ventricular assist device as claimed in claim 19; wherein the bias flux shifts according to movement of the plate which results in a negative spring force generated by a magnetic field induced thereby, and wherein the compressible chambers possess an elasticity that acts in opposition to the negative spring.

30. A ventricular assist device as claimed in claim 19, wherein each of the chambers has an elasticity, further comprising springs disposed between the frame and the plate and augmenting the elasticity of the chambers.

31. A device for assisting the cardiovascular system of a patient, the cardiovascular system including an arterial vessel and a heart having a ventricle with an ejection volume, the device comprising:
    a pump including:
        a frame;
        a pair of coils including a first coil and a second coil disposed in a spaced relationship within the frame, the coils generating coil flux and defining a pair of poles including a first pole and a second pole when electrically activated;
        a plate including an armature and a magnet, the plate being disposed within the frame such that the armature is between the poles; and
        a pair of compressible chambers including a first chamber and a second chamber respectively disposed between the plate and each of the coils, each of the chambers having a volume less than about one-half of the ejection volume of the ventricle; and
    cannulation for connecting the pump to the cardiovascular system of the patient.

32. A device as claimed in claim 31, wherein each of the chambers has a volume of about one-quarter the ejection volume of the ventricle.

33. A device as claimed in claim 31, wherein the cannulation comprises:
    an inlet conduit connected to the pump to be in communication with the chambers for receiving blood from the ventricle; and
    an outlet conduit connected to the pump to be in communication with the chambers for delivering blood to an artery of the patient.

34. A device as claimed in claim 33, wherein each of the chambers is connected to the inlet conduit and the outlet conduit such that each of the chambers receives blood when the other the chamber ejects blood.

35. A device as claimed in claim 33, wherein one of the chambers is connected to the inlet conduit and the other chamber is connected to the outlet conduit; the pump further including a transfer conduit connected between the chambers.

36. A device as claimed in claim 31, wherein the pump is substantially cylindrical with an external diameter of less than about 100 millimeters.

37. A device as claimed in claim 31, further comprising a controller connected to supply current to the electromagnetic coils, and an input sensor positioned in the inlet conduit and connected to provide physiological data to the controller, the controller supplying current to the coils based on the physiological data so provided.

38. A device as claimed in claim 37, wherein the input sensor senses pressure in the inlet conduit and the controller causing the coils to continuously move the plate when the pressure sensed is above a threshold value.

39. A method of ventricular assist, comprising:
    providing a ventricular assist pump including two pumping chambers, valved inlet and outlet conduits for each chamber, and an actuator;
    directing an inflow of blood from a single ventricle to both of the chambers; and
    actuating the pumping chambers with the actuator during a systolic phase of the assisted ventricle to alternately expel blood from one of the chambers while drawing blood into the other of the chambers.

40. The method of claim 39, further including resting the pumping chambers during the diastolic phase.

41. The method of claim 40, further including sensing the pressure of the ventricle and controlling actuation of the pumping chambers based on the pressure sensed.

42. The method of claim 39, wherein the actuator is an armature and the pump includes coils for generating a coil flux to displace the armature, and wherein the actuator further includes a bias magnet generating a bias flux, the pump being configured so that a portion of the path of the coil flux interacts with a portion of the path of the bias flux.

43. A method of ventricular assist, comprising:
    providing a positive displacement pulsatile pump having two variable-volume chambers each with a volume less than about one-half of the ejection volume of the ventricle;
    implanting the pump in a patient so as to be in fluid communication with the blood circulatory system;
    actuating the pump during systole to provide substantially continuous flow output and propel the ventricular ejection volume into an arterial vessel; and
    resting the pump during a diastolic phase of the assisted ventricle.

44. The method of claim 43, further including sensing the pressure of the ventricle and controlling actuation of the pump based on the pressure sensed.

* * * * *